United States Patent [19]

Nakamura et al.

[11] Patent Number: 4,642,355
[45] Date of Patent: Feb. 10, 1987

[54] PROLINE DERIVATIVES

[75] Inventors: Shizuo Nakamura, Naruto; Makoto Inoue, Tokushima; Yoshiaki Tsuda, Anan, all of Japan

[73] Assignee: Otsuka Pharmaceutical Factory, Inc., Tokushima, Japan

[21] Appl. No.: 703,365

[22] Filed: Feb. 20, 1985

[30] Foreign Application Priority Data

Feb. 24, 1984 [JP] Japan ................... 59-34701
May 18, 1984 [JP] Japan ................... 59-101588
Jun. 22, 1984 [JP] Japan ................... 59-129893
Feb. 19, 1985 [JP] Japan ................... 60-30834

[51] Int. Cl.$^4$ ............... C07D 207/00; A61K 37/64; C07K 5/06
[52] U.S. Cl. .................................................. 548/533
[58] Field of Search ............... 260/112.5 R; 548/533; 514/19

[56] References Cited

FOREIGN PATENT DOCUMENTS 0012401 6/1980 European Pat. Off. .
0050800 5/1982 European Pat. Off. .
81845 6/1980 Japan .

*Primary Examiner*—Delbert R. Phillips
*Attorney, Agent, or Firm*—Armstrong, Nikaido, Marmelstein & Kubovcik

[57] ABSTRACT

This invention provides a proline derivative represented by the formula

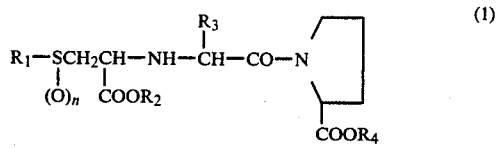

wherein:

$R_1$ is $C_5$–$C_{14}$ alkyl, $C_2$–$C_6$ alkenyl, $C_3$–$C_8$ cycloalkyl-$C_1$–$C_6$ alkyl or a group

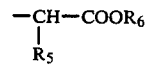

(wherein $R_5$ is hydrogen, $C_1$–$C_{14}$ alkyl or phenyl and $R_6$ is hydrogen or $C_1$–$C_6$ alkyl);
$R_2$ is hydrogen or $C_1$–$C_6$ alkyl;
$R_3$ is $C_1$–$C_6$ alkyl;
$R_4$ is hydrogen, $C_1$–$C_6$ alkyl or phenyl-$C_1$–$C_6$ alkyl; and
n is 0, 1 or 2, and a pharmaceutically acceptable salt thereof.

29 Claims, No Drawings

PROLINE DERIVATIVES

The present invention relates to novel proline derivatives and pharmaceutical compositions containing the proline derivative.

The proline derivatives of the present invention are represented by the formula

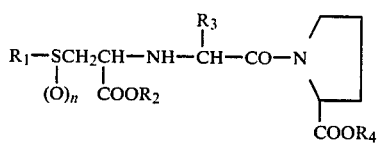

wherein:
$R_1$ is $C_5$–$C_{14}$ alkyl, $C_2$–$C_6$ alkenyl, $C_3$–$C_8$ cycloalkyl-$C_1$–$C_6$ alkyl or a group

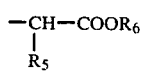

(wherein $R_5$ is hydrogen, $C_1$–$C_{14}$ alkyl or phenyl and $R_6$ is hydrogen or $C_1$–$C_6$ alkyl);
$R_2$ is hydrogen or $C_1$–$C_6$ alkyl;
$R_3$ is $C_1$–$C_6$ alkyl;
$R_4$ is hydrogen, $C_1$–$C_6$ alkyl or phenyl-$C_1$–$C_6$ alkyl; and
n is 0, 1 or 2.

In the specification, the substituents represented by $R_1$ to $R_6$ in the formula (1) are exemplified as follows.

Examples of $C_5$–$C_{14}$ alkyl groups are straight-chain or branched-chain alkyl groups such as pentyl, isopentyl, 2-methylbutyl, 1-methylbutyl, neopentyl, hexyl, 2-methylpentyl, 3-methylpentyl, 4-methylpentyl, 2,2-dimethylbutyl, 3,3-dimethylbutyl, heptyl, octyl, nonyl, decyl, undecyl, dodecyl, tridecyl, tetradecyl, 6-methylheptyl, 7-methyloctyl, 8-methylnonyl, 9-methyldecyl, 10-methylundecyl, 11-methyldodecyl, 12-methyltridecyl, 13-methyltetradecyl and the like.

Examples of $C_2$–$C_6$ alkenyl groups are vinyl, allyl, 2-butenyl, 3-butenyl, 3-methyl-2-butenyl, 1-methylallyl, 2-pentenyl, 2-hexenyl and the like.

Examples of $C_3$–$C_8$ cycloalkyl groups of $C_3$–$C_8$ cycloalkyl-$C_1$–$C_6$ alkyl group are cyclopropyl, cyclobutyl, cyclopentyl, cyclohexyl, cycloheptyl, cyclooctyl and the like. Examples of $C_3$–$C_8$ cycloalkyl-$C_1$–$C_6$ alkyl groups are cyclopropylmethyl, cyclobutylmethyl, cyclopentylmethyl, cyclohexylmethyl, cycloheptylmethyl, cyclooctylmethyl, 1-cyclopentylethyl, 2-cyclopentylethyl, 1-cyclohexylethyl, 2-cyclohexylethyl, 1-cyclohexylpropyl, 2-cyclohexylpropyl, 3-cyclohexylpropyl, 4-cyclohexylbutyl, 5-cyclohexylpentyl, 6-cyclohexylhexyl and the like.

Examples of $C_1$–$C_6$ alkyl groups are methyl, ethyl, propyl, isopropyl, butyl, isobutyl, t-butyl, pentyl, hexyl and the like.

Examples of $C_1$–$C_{14}$ alkyl groups represented by $R_5$ are the same as exemplified above for $C_5$–$C_{14}$ alkyl and $C_1$–$C_6$ alkyl groups.

Examples of phenyl-$C_1$–$C_6$ alkyl groups are benzyl, α-phenethyl, β-phenethyl, 3-phenylpropyl, 4-phenylbutyl, 5-phenylpentyl, 6-phenylhexyl, 1,1-dimethyl-2-phenylethyl, 1-methyl-2-phenylethyl and the like.

The compounds of the formula (1) have asymmetric carbon atoms in the molecule and therefore optical isomers exist. The present invention include all the isomers of the compounds.

The salts of the proline derivatives of the present invention include pharmaceutically acceptable acid addition salts. Examples of acidic compounds useful for forming the acid addition salts are inorganic acids such as hydrochloric acid, sulfuric acid, nitric acid, phosphoric acid, hydrobromic acid and the like, and organic acids such as oxalic acid, maleic acid, fumaric acid, malic acid, tartaric acid, citric acid, benzoic acid, picric acid and the like.

Of the proline derivatives of the present invention, those having one or more acidic groups can be converted into pharmaceutically acceptable salts by being acted on by a base. The proline derivatives of the present invention also include these pharmaceutically acceptable salts. Examples of bases which can be used in the present invention are inorganic bases such as sodium hydroxide, potassium hydroxide, calcium hydroxide, sodium carbonate, potassium hydrogencarbonate and the like and organic bases such as lysine, arginine, ornithine, morpholine, piperazine, piperidine, ethylamine, dimethylamine, triethylamine, dicyclohexylamine and the like.

The proline derivatives of the present invention an salts thereof have an angiotensin converting enzyme-inhibitory action and are useful as a hypotensor. When orally administered, the present proline derivative can be absorbed within a short period of time and can exhibit a sustained effect. Further the present derivatives and salts thereof are of low toxicity and possess an immunity-enhancing effect, expectorant action and action of reducing the intraocular pressure and can be used as an immunostimulant, expectorant or agent for treating glaucoma. Known compounds having angiotensin converting enzyme-inhibitory action include, for example, amino acid derivatives disclosed in Japanese Unexamined Patent Publication No. 81845/1980. Of the present compounds of the formula (1), those wherein $R_1$ is a branched- or straight-chain alkyl group having 5 or 6 carbon atoms (preferably n-pentyl or n-hexyl), n is 0, $R_4$ is hydrogen or $C_1$–$C_6$ alkyl and $R_2$ and $R_3$ are as defined above may fall within the scope of the formula representing the amino acid derivatives of Publication No. 81845/1980, but are not specifically disclosed in the Publication. Moreover, the present compounds as specified above are superior in angiotensin converting enzyme-inhibitory action to the compounds specifically indicated in the Publication and can produce the action in a shorter period of time than the latter. The present derivatives outside the foregoing scope are novel compounds undisclosed in the Publication.

The proline derivatives of the present invention and intermediates for preparing the present derivatives can be produced, for example, by processes shown below in the following reaction schemes.

Reaction Scheme-1

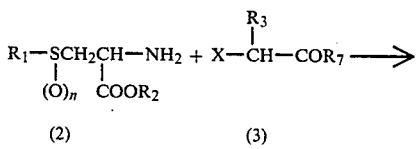

-continued
Reaction Scheme-1

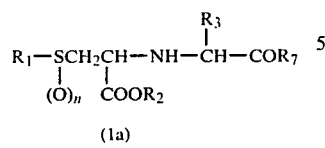

(1a)

In the foregoing formulas, $R_1$, $R_2$, $R_3$ and n are as defined above and $R_7$ are hydroxyl, $C_1$–$C_6$ alkoxy or a group

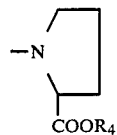

(wherein $R_4$ is as defined above) and X is halogen, alkylsulfonyloxy or arylsulfonyloxy.

Exemplary of halogen atoms represented by X in the propionic acid derivative of the formula (3) are chlorine, bromine, iodine and the like. Representative of alkylsulfonyloxy groups in the derivative of the formula (3) are methanesulfonyloxy, ethanesulfonyloxy and the like. Illustrative of arylsulfonyloxy in the derivative are p-toluenesulfonyloxy, benzenesulfonyloxy and the like.

According to the process as shown in Reaction Scheme-1, the cysteine derivative (2) is condensed with the propionic acid derivative (3), whereby a compound (1a) is given. The condensation reaction is conducted in a suitable solvent in the presence of an acid binder. Examples of useful solvents are alcohols such as methanol, ethanol, 2-propanol, t-butanol and the like; ethers such as diethyl ether, tetrahydrofuran (THF), dioxane and the like; and aprotic polar solvents such as dimethylformamide (DMF), dimethyl sulfoxide (DMSO), hexamethylphosphoric triamide (HMPA) and the like. Examples of useful acid binders are alkali metal carbonates such as sodium carbonate, potassium carbonate and alkali meal hydrogencarbonate such as sodium hydrogencarbonate, potassium hydrogencarbonate and the like; organic tertiary amines such as triethylamine, pyridine, 1,8-diazabicyclo 5,4,0 undecan-7-ene (DBU) and the like. The acid binder is generally used in an amount of about 1 to about 2 moles, preferably about 1 to about 1.2 moles, per mole of the cysteine derivative (2). The propionic acid derivative (3) is generally used in an amount of at least 1 mole, preferably about 1 to about 1.2 moles, per mole of the cysteine derivative (2). The reaction is carried out at usually about 0° to about 80° C., preferably at or near room temperature and is completed in about 3 to about 72 hours.

The cysteine derivative (2) to be used as the starting material in the foregoing reaction can be synthesized by the processes described, for example, in J. Org. Chem., 16, 749 (1959), Helv. Chim. Acta., 32, 866 (1949), J. Biol., Chem., 140, 131 (1941), etc.

Reaction Scheme-2

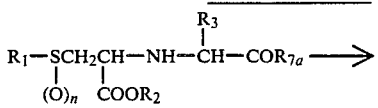

(1a')

-continued
Reaction Scheme-2

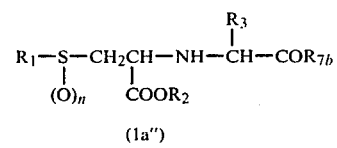

(1a'')

In the foregoing formulas, $R_1$, $R_2$, $R_3$ and n are as defined above, $R_{7a}$ is $C_1$–$C_6$ alkoxy or a group

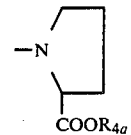

(wherein $R_{4a}$ is $C_1$–$C_6$ alkyl or phenyl-$C_1$–$C_6$ alkyl) and $R_{7b}$ is hydroxyl or a group

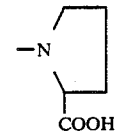

According to the process as shown in Reaction Scheme-2, the compound (1a'') can be prepared by treating the compound (1a') with an acid in the presence of a scavenger such as anisole, thioanisole, dimethylsulfide and the like.

Examples of acids useful in the acid treatment are organic acids such as acetic acid, trifluoroacetic acid (TFA), methanesulfonic acid, trifluoromethanesulfonic acid and the like, and inorganic acids such as hydrochloric acid, hydrobromic acid, hydrofluoric acid and the like. The reaction can be performed in a solvent, suitable examples being ethers such as diethyl ether, THF, dioxane and the like; esters such as methyl acetate, ethyl acetate and the like; and halogenated hydrocarbons such as methylene chloride, chloroform and the like. When trifluoroacetic acid is used as the acid, the solvent is not needed. Accordingly the use of this acid is preferred. The scavenger such as anisole is used in an amount of usually about 1 to about 10 moles, preferably about 3 to about 5 moles, per mole of the compound (1a'). The reaction is conducted at about 0° to about 50° C., preferably about 0° to about 25° C. and is completed in about 1 to about 10 hours.

Reaction Scheme-3

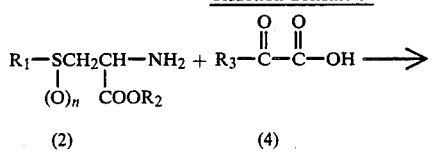

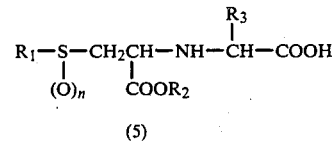

(5)

In the foregoing formulas, $R_1$, $R_2$, $R_3$ and n are as defined above.

According to Reaction Scheme-3, the compound (5) can be prepared by reacting the cysteine derivative (2) with the α-keto acid (4). This reaction is a reductive bond-forming reaction using complex metal hydrides, and can be conducted by reducing a Schiff base formed by the reaction of the cysteine derivative (2) with the α-keto acid (4) in the presence of the complex metal hydrides. Examples of complex metal hydrides are sodium borohydride, lithium borohydride, sodium cyanoborohydride, lithium cyanoborohydride and the like. The complex is used usually in an amount of about 2 to about 6 moles, preferably about 2 to about 3 moles, per mole of the cysteine derivative (2). The α-keto acid (4) is used in an amount of about 1 to about 10 moles, preferably about 3 to about 5 moles, per mole of the cysteine derivative (2). The reaction is carried out in an inert solvent which does not adversely affect the reaction. Examples of useful solvents are water; alcohols such as ethanol, methanol, 2-propanol and the like; ethers such as diethyl ether, THF, dioxane and the like; aprotic polar solvents such as DMF, DMSO and the like. These solvents can be used singly or at least two of them are usable in admixture. The reaction is conducted usually at 0° to about 50° C., preferably at or near room temperature and is completed in about 3 to about 24 hours. When using sodium cyanoborohydride or lithium cyanoborohydride, the reaction rapidly proceeds at a pH of about 6.5 to about 8.5, preferably around a neutral pH range.

Reaction Scheme-4

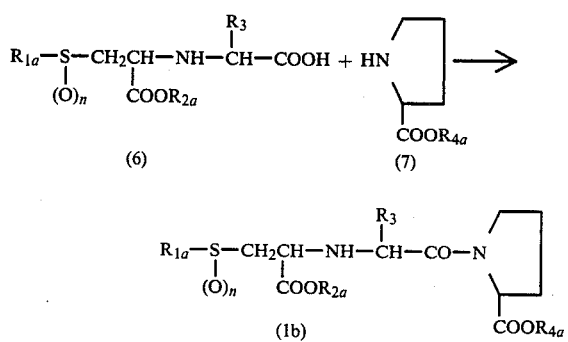

(6)   (7)

→

(1b)

In the forgoing formulas, $R_3$ and n are as defined above, $R_{1a}$ is $C_5$–$C_{14}$ alkyl, $C_2$–$C_6$ alkenyl, $C_3$–$C_8$ cycloalkyl-$C_1$–$C_6$ alkyl or a group

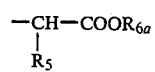

(wherein $R_{6a}$ is $C_1$–$C_6$ alkyl and $R_5$ is as defined above), $R_{2a}$ is $C_1$–$C_6$ alkyl, $R_{4a}$ is $C_1$–$C_6$ alkyl or phenyl-$C_1$–$C_6$ alkyl.

According to Reaction Scheme-4, the compound (1b) of the present invention is produced by reacting the carboxylic acid (6) obtained in Reaction Schemes 1 to 3 with the amine (7). The reaction can be conducted by various processes according to the conventional amide bond-forming reaction, for example as shown below.

(i) A condensation reaction in which the carboxylic acid (6) is condensed with the amine (7) in the presence of a condensing agent.

(ii) A mixed anhydride method in which the carboxylic acid (6) is reacted with an alkyl haloformate to obtain a mixed anhydride with which the amine (7) is reacted.

(iii) An activated ester method in which the carboxylic acid (6) is made into an active ester such as p-nitrophenyl ester, N-hydroxy succinimide ester, N-hydroxy-5-norbornene-2,3-dicarboximide ester and the like which is then reacted with the amine (7).

(iv) A carboxylic acid halide method in which the halide of carboxylic acid (6) is reacted with the amine (7).

(v) Other processes

The carboxylic acid (6) is treated with a dehydrating agent such as acetic anhydride to obtain an acid anhydride with which the amine (7) is reacted. It is also possible as another option to react the amine (7) with an ester of the carboxylic acid (6) formed by use of a lower alcohol.

The processes described above (i)–(v) can be carried out under substantially the same conditions as in conventional respective processes. Of the foregoing processes, the process (i) is preferred and hereinafter described in detail. The process (i) employs as a condensing agent N,N'-dicyclohexylcarbodiimide (DCC), DCC-N-hydroxysuccinimide, DCC-N-hydroxybenzotriazole, DCC-N-hydroxy-5-norbornene-2,3-dicarboximide, diphenylphosphorylazide (DPPA)-triethylamine, diethyl phosphorocyanidate (DEPC)-triethylamine, etc. The reaction is conducted generally in a suitable solvent. Useful solvents can be any of various conventional solvents which do not adversely affect the reaction. Examples of suitable solvents are halogenated hydrocarbons such as methylene chloride, chloroform, dichloroethane and the like; aromatic hydrocarbons such as benzene, toluene, xylene and the like; ethers such as diethyl ether, THF, dioxane and the like; esters such as methyl acetate, ethyl acetate and the like, and aprotic polar solvents such as DMF, DMSO, HMPA and the like. The amount of the amine (7) used is usually at least about 1 mole, preferably about 1 to about 1.2 moles, per mole of the carboxylic acid (6). The condensing agent is used in an amount of about 1 to about 2 moles, preferably about 1 to about 1.2 moles, per mole of the carboxylic acid (6). The reaction is conducted at generally about −20 to about 30° C., preferably about −10° C. to room temperature, and is completed in about 3 to about 24 hours.

Reaction Scheme-5

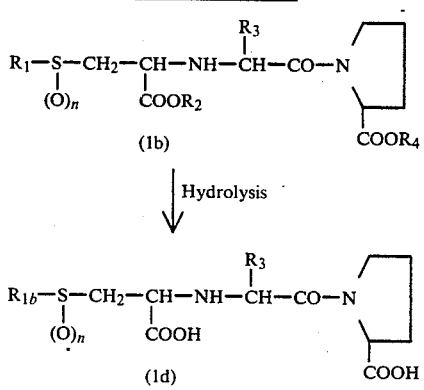

(1b)

↓ Hydrolysis (1d)

In the foregoing formulas, $R_1$, $R_2$, $R_3$, $R_4$ and n are as defined above, $R_{1b}$ is $C_5-C_{14}$ alkyl, $C_2-C_6$ alkenyl, $C_3-C_8$ cycloalkyl-$C_1-C_6$ alkyl or

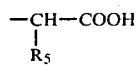

(wherein $R_5$ is as defined above), with the proviso that in the formula (1b), $R_2$, $R_4$ and $R_6$ are not hydrogen at the same time.

According to Reaction Scheme-5, the compounds of the formula (1) wherein $R_2$, $R_4$ and $R_6$ are hydrogen, i.e., the compound (1d), is prepared by hydrolysis of the compound (1b) of the present invention wherein at least one of $R_2$, $R_4$ and $R_6$ constitutes an ester. This hydrolysis is conducted in a suitable solvent and in the presence of a basic compound. Examples of useful solvents are mixtures of water and an organic solvent, e.g., lower alcohols such as methanol, ethanol and the like; ethers such as diethyl ether, THF, dioxane and the like; and acetonitrile and the like. Examples of basic compounds useful in the foregoing reaction are alkali metal hydroxides such as sodium hydroxide, potassium hydroxide, lithium hydroxide and the like. When $R_1$ is $C_5-C_{14}$ alkyl, $C_2-C_6$ alkenyl, $C_3-C_8$ cycloalkyl-$C_1-C_6$ alkyl, the basic compound is generally used in an amount of about 2 to about 3 moles, preferably about 2 to about 2.2 moles, per mole of the the present compound (1b). When $R_1$ is

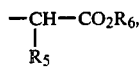

the basic compound is generally used in an amount of about 3 to about 4 moles, preferably about 3 to about 3.3 moles, per mole of the present compound (1b). The reaction is performed at usually 0° to about 40° C., preferably below room temperature and is completed in about 0.5 to about 12 hours.

The desired compounds obtained in the reactions in Reaction Schemes-1 to 5 can be easily separated from the reaction mixture and purified by the conventional separation methods including solvent extraction, dilution, distillation and recrystallization methods, column chromatography, preparative thin-layer chromatography, ion-exchange chromatography, gel chromatography, etc.

For use as pharmaceuticals, the compound of the invention is administered to humans as it is or as formulated into pharmaceutical compositions in combination with conventional pharmaceutically acceptable carriers. Examples of useful carriers are those conventionally used for preparing pharmaceutical compositions in the desired form, such as diluents and excipients including a filler, extender, binder, wetting agent, disintegrator, surfactant and glazing agent.

The pharmaceutical compositions can be in any of various dosage forms in accordance with the contemplated purpose of treatment. Typically they are in the form of tablets, pills, powders, solutions, suspensions, emulsions, granules, capsules, suppositories, injections (solutions, suspensions, etc.), etc. For the preparation of tablets, extensive use may be made of carriers already known in the art. Useful examples are excipients such as lactose, white sugar, sodium chloride, glucose solution, urea, starch, calcium carbonate, kaolin, crystalline cellulose and silicic acid; binders such as water, ethanol, propanol, syrup, glucose, starch solution, gelatin solution, carboxymethyl cellulose, shellac, methyl cellulose, potassium phosphate and polyvinyl pyrrolidone; disintegrators such as dried starch, sodium alginate, agar powder, laminaria powder, sodium hydrogencarbonate, calcium carbonate, Tween, sodium lauryl sulfate, glyceryl monostearate, starch and lactose; disintegration suppressants such as white sugar, stearin, cacao butter and hydrogenated oils; absorption promoters such as quaternary ammonium salt and sodium lauryl sulfate; humectants such as glycerin and starch; adsorbents such as starch, lactose, kaolin, bentonite and colloidal silicic acid; glazing agents such as purified talc, stearic acid salts, boric acid powder and polyethylene glycol; etc. For the preparation of pills, a wide variety of carriers are usable which are already known in the art, useful examples being excipients, such as glucose, lactose, starch, cacao fat, hardened vegetable oils, kaolin and talc; binders such as gum arabic powder, tragacanth powder, gelatin and ethanol; disintegrators such as laminaria and agar; etc. When desired, tablets can be provided with a usual coating. Thus useful are sugar-coated, gelatin-coated, enteric coated, film-coated, double-layer and multiple-layer tablets. Suppositories may be formulated with use of a wide variety of known carriers, such as polyethylene glycol, cacao fat, higher alcohols, esters of higher alcohols, gelatin and semi-synthetic glycerides. The solutions and suspensions for injection should be sterilized and are preferably isotonic with the blood. For the preparation of such solutions, emulsions and suspensions, any diluent is usable which is usually used in the art. Examples of useful diluents are water, ethyl alcohol, propylene glycol, ethoxylated isostearyl alcohol, polyoxyisostearyl alcohol, polyoxyethylene sorbitol, sorbitan esters and the like. For the preparation of pharmaceutical solutions, sodium chloride, glucose or glycerin may be incorporated therein in an amount sufficient to render the solution isotonic. Such solutions may further incorporate usual solubilizing agents, buffers, analgesics, preservatives, etc. The pharmaceutical compositions may contain coloring agents, preservatives, perfumes, flavoring agents, sweetening, etc. as well as other drugs.

The amount of the compound of this invention to be contained in the pharmaceutical compositions is not specifically limited but can be suitably determined over a wide range. Usually the amount is about 1 to about 70% by weight, preferably about 1 to about 30% by weight, of the whole composition. It is preferred that the pharmaceutical compositions in any dosage form each contain about 1 to about 500 mg of the compound of the invention.

The pharmaceutical compositions are not specifically limited in the mode of administration but can be given by a suitable method in accordance with the particular form of the composition. For example, tablets, pills, solutions, suspensions, emulsions, granules and capsules are administered orally. Injections are given intravenously, singly or as admixed with an auxiliary solution of glucose, amino acids, etc. When desired, injections are singly given intramuscularly, intradermally, subcutaneously or intraperitoneally. Suppositories are given to the rectum.

The pharmaceutical compositions are given at a dose suitably determined according to the purpose, symptoms, method of administration, age and sex of the patient, etc. Usually the compositions are administered in an amount of about 0.06 to 50 mg/kg body weight/day, calculated as the present compound, in 1 to 3 divided doses.

Given below are reference examples for preparing the starting compounds to be used for producing the compounds of the present invention and examples for preparing the compounds of the present invention. In the examples and reference examples, the terms "α- and β-ismoers" and "A- and B-isomers" are used to mean the following:

(i) Of 2 isomers produced as the reaction products of ethyl ester of S-alkyl-L-cysteine and t-butyl 2-bromopropionate, a first eluate obtained in silica gel column chromatography (using ether/n-haxane) is hereinafter referred to as "α-isomer", and a second eluate therefrom as "β-isomer". Also hereinafter the compounds prepared from an α-isomer are called "α-isomers" and those from a β-isomer are called "β-isomers".

(ii) Of 2 or 4 isomers produced as the reaction products of ethyl ester of S-[1-ethoxycarbonylalkyl]-L-cysteine and t-butyl 2-bromopropionate, a first eluate separated in silica gel column chromatography (using ether/n-hexane) is hereinafter referred to as "A-isomer" and a second eluate separated therein as "B-isomer". Also hereinafter the compounds prepared from an A-isomer are called "A-isomers", and those from a B-isomer are called "B-isomers".

REFERENCE EXAMPLE 1

Preparation of t-butyl ester of N-[(R)-1-ethoxycarbonyl-2-hexylthioethyl]-alanine (α- and β-isomers)

A 1.5 ml quantity of triethylamine was added to a solution of 2.5 g of ethyl ester of S-hexyl-L-cysteine and 2.3 g of t-butyl 2-bromopropionate in 6 ml of HMPA. The mixture was stirred at room temperature for 24 hours. The reaction mixture was poured into ice water and the mixture was extracted with ethyl acetate. The extract was sufficiently washed with water and dried over anhydrous sodium sulfate. The solvent was evaporated off under reduced pressure and the residue was separated and purified by silca gel column chromatography (a 1:2 mixture of ether and n-hexane as an eluent), producing the α-isomer of the title compound as a colorless oil from the first eluate. Yield 1.2 g.

$[\alpha]_D^{21} = +27.3°$ (c=1.2, ethanol).

$^1$H-NMR (CDCl$_3$): δ: 0.88 (3H, t, J=5 Hz), 1.27 (3H, d, J=7 Hz), 1.29 (3H, t, J=7 Hz), 1.4–1.8 (8H, m), 1.45 (9H, s), 2.55 (2H, t, J=7 Hz), 2.80 (2H, d, J=6 Hz), 3.32 (1H, q, J=7 Hz), 3.46 (1H, t, J=7 Hz), 4.20 (2H, q, J=7 Hz).

The β-isomer of the title compound was obtained as a colorless oil from the second eluate.

Yield 1.1 g.

$[\alpha]_D^{21} = -40.4°$ (c=0.8, ethanol).

$^1$H-NMR (CDCl$_3$): δ: 0.89 (3H, t, J=5 Hz), 1.29 (3H, t, J=7 Hz), 1.29 (3H, d, J=7 Hz), 1.4–1.8 (8H, m), 1.47 (9H, s), 2.54 (2H, t, J=7 Hz), 2.70 (1H, d-d, J=13 Hz, 7.5 Hz), 2.92 (1H, d-d, J=13 Hz, 5 Hz), 3.29 (1H, q, J=7 Hz), 3.47 (1H, d-d, J=7.5 Hz, 5 Hz), 4.21 (2H, q, J=7 Hz).

REFERENCE EXAMPLE 2

Preparation of t-butyl ester of N-[(R)-1-ethoxycarbonyl-2-pentylthioethyl]-alanine (α- and β-isomers)

The α-isomer of the title compound was produced as a colorless oil from the first eluate by following the general procedure of Reference Example 1 and using 8.6 g of ethyl ester of S-pentyl-L-cysteine, 8.2 g of t-butyl 2-bromopropionate and 5.5 ml of triethylamine. Yield 3.9 g.

$[\alpha]_D^{25} = +28.6°$ (c=1.0, ethanol).

$^1$H-NMR (CDCl$_3$): δ: 0.90 (3H, t, J=5.5 Hz), 1.28 (3H, d, J=7 Hz), 1.29 (3H, t, J=7 Hz), 1.45 (9H, s), 1.3–1.8 (6H, m), 2.56 (2H, t, J=7 Hz), 2.81 (2H, d, J=6 Hz), 3.32 (1H, q, J=7 Hz), 3.46 (1H, t, J=6 Hz), 4.20 (2H, q, J=7 Hz).

Second eluate (β-isomer).

Yield 3.6 g.

$[\alpha]_D^{25} = -42.2°$ (c=1.0, ethanol).

$^1$H-NMR (CDCl$_3$): δ: 0.90 (3H, t, J=5.5 Hz), 1.30 (3H, d, J=7 Hz), 1.30 (3H, t, J=7 Hz), 1.47 (9H, s), 1.3–1.8 (6H, m), 2.23 (1H, br s), 2.54 (2H, t, J=7 Hz), 2.70 (1H, d-d, J=13 Hz, 8 Hz), 2.92 (1H, d-d, J=13 Hz, 5.5 Hz), 3.29 (1H, q, J=7 Hz), 3.45 (1H, d-d, J=8 Hz, 5.5 Hz), 4.21 (2H, q, J=7 Hz).

REFERENCE EXAMPLE 3

Preparation of N-[(R)-1-ethoxycarbonyl-2-hexylthioethyl]-alanine (α-isomer)

A 800 mg quantity of the α-isomer of t-butyl ester of N-[(R)-1-ethoxycarbonyl-2-hexylthioethyl]-alanine obtained in Reference 1 was dissolved in 5 ml of TFA and the solution was stirred at room temperature for 3 hours. The TFA was distilled off under reduced pressure and the residue was poured into ice water. The mixture was adjusted to a pH of 4 with a saturated aqueous solution of sodium hydrogencarbonate and the resulting mixture was extracted with methylene chloride. The extract was washed with water and dried over anhydrous sodium sulfate. The solvent was evaporated off under reduced pressure and the residue was recrystallized from methylene chloride, giving the α-isomer of the title compound. Yield 580 mg. M.p. 134°–136° C.

$[\alpha]_D^{21} = +20.9°$ C. (c=0.6, DMF).

REFERENCE EXAMPLES 4–6

The compounds as listed below in Table 1 were obtained by following the general procedure of Reference Example 3.

TABLE 1

$$R_1-S-CH_2\overset{(R)}{C}H-NH-\overset{\overset{CH_3}{|}}{\underset{*}{C}H}-CO_2H$$
$$|$$
$$CO_2C_2H_5$$

| Ref. Ex. No. | R$_1$ | Isomer (*) | Optical Rotation (Solvent: DMF) | Melting point (°C.) |
|---|---|---|---|---|
| 4 | CH$_3$(CH$_2$)$_5$— | β | $[\alpha]_D^{21} = -26.6°$ (c = 0.7) | 130–132.5 |
| 5 | CH$_3$(CH$_2$)$_4$— | α | $[\alpha]_D^{21} = +21.9°$ (c = 0.9) | 134–136 |
| 6 | CH$_3$(CH$_2$)$_4$— | β | $[\alpha]_D^{21} = -28.1°$ (c = 0.9) | 124–125 |

REFERENCE EXAMPLE 7

Preparation of N-[(R)-1-ethoxycarbonyl-2-hexylthioethyl]-(R,S)-alanine

A solution of 1.4 g of ethyl ester of S-hexyl-L-cysteine in 25 ml of ethanol was mixed with 10 ml of water. A 2.6 g quantity of pyruvic acid was added with ice cooling to the mixture. The resulting mixture was adjusted to a pH of 7 with a 4N aqueous solution of sodium hydroxide. A 750 mg quantity of sodium cyanoborohydride was gradually added to the mixture, and the resulting admixture was stirred at room temperature for 14 hours. The solvent was distilled off under reduced pressure and the residue was dissolved in a saturated aqueous solution of sodium hydrogencarbonate to obtain a weakly alkaline solution. The solution was washed with ether and the aqueous layer was adjusted to a pH of 4 with a 1N solution of hydrochloric acid and the mixture was extracted with ethyl acetate. The extract was sufficiently washed with water and dried over anhydrous sodium sulfate and the solvent was evaporated off under reduced pressure, giving 1.5 g of the title compound.

EXAMPLE 1

Preparation of t-butyl ester of N-[(R)-1-ethoxycarbonyl-2-hexylthioethyl]-alanyl-(S)-proline (α-isomer)

A solution of 650 mg of DEPC (90% content) in 2 ml of DMF was added with ice cooling to a solution of 1.0 g of the N-[(R)-1-ethoxycarbonyl-2-hexylthioethyl]-alanine (α-isomer) obtained in Reference Example 3 and 620 mg of t-butyl ester of (S)-proline in 10 ml of DMF. A solution of 0.5 ml of triethylamine in 2 ml of DMF was gradually added dropwise thereto. The mixture was stirred with ice cooling for 2 hours and further at room temperature for 10 hours. The reaction mixture was poured into ice water and the mixture was rendered weakly alkaline by the addition of a saturated aqueous solution of sodium hydrogencarbonate. The mixture was extracted with ethyl acetate. The extract was sufficiently washed with water and dried over anhydrous sodium sulfate. The extract was distilled under reduced pressure and the residue was purified by silica gel column chromatography (using a 30:1 mixture of chloroform and methanol as an eluent), giving the α-isomer of the title compound as a colorless oil. Yield 1.5 g.

$[\alpha]_D^{21} = -28.2°$ (c=0.8, ethanol).

$^1$H-NMR (CDCl$_3$): δ: 0.88 (3H, t, J=5 Hz), 1.2–1.5 (6H, m), 1.45, 1.46 (total 9H, each s), 1.2–1.8 (8H, m), 1.8–2.5 (4H, m), 2.5–3.0 (4H, m), 3.4–3.9 (4H, m), 4.1–4.5 (3H, m).

EXAMPLE 2

Preparation of t-butyl ester of N-[(R)-1-ethoxycarbonyl-2-hexylthioethyl]-alanyl-(S)-proline (β-isomer)

The general procedure of Example 1 was followed using 1.0 g of the N-[(R)-1-ethoxycarbonyl-2-hexylthioethyl]-alanine (β-isomer) obtained in Reference Example 4, thereby producing 1.4 g of the β-isomer of the title compound as a colorless oil.

$[\alpha]_D^{21} = -97.2°$ (c=0.9, ethanol).

$^1$H-NMR (CDCl$_3$): δ: 0.88 (3H, t, J=5 Hz), 1.29 (3H, t, J=7 Hz), 1.29 (3H, d, J=6.5 Hz), 1.44, 1.46 (total 9H, each s), 1.2–1.8 (8H, m), 1.8–2.2 (4H, m), 2.54 (2H, t, J=7 Hz), 2.70 (1H, d-d, J=13 Hz, 7.5 Hz), 2.92 (1H, d-d, J=13 Hz, 5 Hz), 3.2–3.7 (4H, m), 4.20 (2H, q, J=7 Hz), 4.3–4.5 (1H, m).

EXAMPLE 3

Preparation of t-butyl ester of N-[(R)-1-ethoxycarbonyl-2-pentylthioethyl]-alanyl-(S)-proline (β-isomer)

The general procedure of Example 1 was followed using 1.5 g of the N-[(R)-1-ethoxycarbonyl-2-pentylthioethyl]-alanine (β-isomer) obtained in Reference Example 6, thereby giving 2.2 g of the β-isomer of the title compound as a colorless oil.

$[\alpha]_D^{21} = -94.3°$ (c=1.0, ethanol).

$^1$H-NMR (CDCl$_3$): δ: 0.89 (3H, t, J=5.5 Hz), 1.29 (3H, t, J=7 Hz), 1.29 (3H, d, J=7 Hz), 1.44, 1.47 (total 9H, each s), 1.3–1.8 (6H, m), 1.8–2.3 (4H, m), 2.52 (2H, t, J=7 Hz), 2.68 (1H, d-d, J=13 Hz, 7 Hz), 2.90 (1H, d-d, J=13 Hz, 6 Hz), 3.31 (1H, q, J=7 Hz), 3.58 (1H, d-d, J=7 Hz, 6 Hz), 3.4–3.7 (2H, m), 4.20 (2H, q, J=7 Hz), 4.3–4.5 (1H, m).

EXAMPLE 4

Preparation of N-[(R)-1-ethoxycarbonyl-2-hexylthioethyl]-alanyl-(S)-proline (α-isomer) and L-arginine salt thereof In 4 ml of TFA were dissolved 670 mg of the t-butyl ester of N-[(R)-1-ethoxycarbonyl-2-hexylthioethyl]-alanyl-(S)-proline (α-isomer) and 0.5 ml of anisole. The solution was stirred at room temperature for 2.5 hours. The TFA was distilled off under reduced pressure, and the residue was dissolved in a saturated aqueous solution of sodium hydrogencarbonate to adjust its pH to 8. The solution was washed with ether, the aqueous layer was adjusted to a pH of 4 with a 1N solution of hydrochloric acid and extracted with methylene chloride. The extract was washed with water and dried over anhydrous sodium sulfate, and the solvent was evaporated off under reduced pressure, giving the α-isomer of the title compound as a colorless oil. Yield 540 mg.

A 500 mg quantity of the α-isomer obtained above was dissolved in 10 ml of ethanol and a solution of 217 mg of L-arginine in 4 ml of water was added to the solution. The solvent was distilled off under reduced pressure. Ethanol was added to the residue and distilled off under reduced pressure and this procedure was repeated several times. Anhydrous ether was added to the residue, and the precipitated crystals were filtered, giving L-arginine salt of the title compound.

Yield 580 mg. M.p. 63°–65° C.

$[\alpha]_D^{20} = -32.7°$ (c=0.8, ethanol).

EXAMPLE 5

Preparation of N-[(R)-1-ethoxycarbonyl-2-hexylthioethyl]-alanyl-(S)-proline (β-isomer) and L-arginine salt thereof The general procedure of Example 4 was followed using 690 mg of the t-butyl ester of N-[(R)-1-ethoxycarbonyl-2-hexylthioethyl]-alanyl-(S)-proline (β-isomer) obtained in Example 2, thereby giving the β-isomer of the title compound as a colorless oil.

Yield 520 mg.

L-arginine salt of the title compound.

M.p. 73°–76° C.

$[\alpha]_D^{20} = -61.7°$ (c=0.8, ethanol).

EXAMPLE 6

Preparation of
N-[(R)-1-ethoxycarbonyl-2-pentylthioethyl]-alanyl-(S)-proline (β-isomer) and L-arginine salt thereof The β-isomer of the title compound was produced as a colorless oil from 660 mg of the t-butyl ester of N-[(R)-1-ethoxycarbonyl-2-pentylthioethylalanyl]-(S)-proline (β-isomer) obtained in Example 3 by following the general procedure of Example 4. Yield 590 mg.

L-arginine salt of the title compound.
M.p. 72°–80° C.
$[\alpha]_D^{21} = -38.2°$ (c=0.8, ethanol).

EXAMPLE 7

Preparation of t-butyl ester of
N-[(R)-1-ethoxycarbonyl-2-hexylthioethyl]-(R,S)-alanyl-(S)-proline The title compound was produced as a colorless oil from 1.0 g of the N-[(R)-1-ethoxycarbonyl-2-hexylthioethyl]-(R,S)-alanine obtained in Reference Example 7 by following the general procedure of Example 1. Yield 1.4 g.

$[\alpha]_D^{21} = -61.0°$ (c=1.0, ethanol).

$^1$H-NMR (CDCl$_3$): δ: 0.88 (3H, t, J=5 Hz), 1.2–1.4 (6H, m), 1.44, 1.49 (total 9H, each s), 1.2–1.8 (8H, m), 1.8–2.3 (4H, m), 2.3–2.9 (4H, m), 3.3–3.8 (4H, m), 4.0–4.5 (3H, m).

EXAMPLE 8

Preparation of
N-[(R)-1-ethoxycarbonyl-2-hexylthioethyl]-(R,S)-alanyl-(S)-proline and L-arginine salt thereof The general procedure of Example 4 was followed using 600 mg of the t-butyl ester of N-[(R)-1-ethoxycarbonyl-2-hexylthioethyl]-(R,S)-alanyl-(S)-proline obtained in Example 7, 0.41 ml of anisole and 4 ml of TFA, thereby giving 480 mg of the title compound as a colorless oil.

L-arginine salt of the title compound.
M.p. 55°–65° C.
$[\alpha]_D^{21} = -39.5°$ (c=0.7, ethanol).

EXAMPLE 9

Preparation of
N-[(R)-1-carboxy-2-hexylthioethyl]-alanyl-(S)-proline (α-isomer)

A 3.2 ml quantity of a 1N aqueous solution of sodium hydroxide was added with ice cooling and stirring to a solution of 600 mg of the N-[(R)-1-ethoxycarbonyl-2-hexylthioethyl]-alanyl-(S)-proline (α-isomer) obtained in Example 4 in 8 ml of ethanol. The mixture was stirred at room temperature for 2.5 hours, and applied to a column (Dowex 50W-X8(H+)). The reaction product was sufficiently washed with water, and eluted with a 4% aqueous solution of pyridine. Fractions of the title compound were collected and lyophilized. The powder thus obtained was reprecipitated with ethanolether, giving the title compound. Yield 270 mg.
M.p. 109°–112° C.
$[\alpha]_D^{21} = -45.6°$ (c=0.6, ethanol).

EXAMPLES 10–12

The compounds as listed below in Table 2 were produced by following the general procedure of Example 9.

TABLE 2

$$R_1-S-CH_2\overset{(R)}{C}H-NH-\overset{CH_3}{\underset{*}{C}H}-CO-N\overset{(S)}{\diagdown}$$
$$\underset{CO_2H}{|} \qquad\qquad \diagdown CO_2H$$

| Example No. | R$_1$ | Isomer (*) | Optical Rotation (Solvent: ethanol) | Melting point (°C.) |
|---|---|---|---|---|
| 10 | CH$_3$(CH$_2$)$_5$— | β | $[\alpha]_D^{20} = -109.6°$ (c = 0.6) | 73–77 |
| 11 | CH$_3$(CH$_2$)$_5$— | RS | $[\alpha]_D^{22} = -77.5°$ (c = 0.7) | 66–78 |
| 12 | CH$_3$(CH$_2$)$_4$— | β | $[\alpha]_D^{23} = -104.7°$ (c = 0.4) | 76–83 |

REFERENCE EXAMPLE 8

Preparation of t-butyl ester of
N-[(R)-1-ethoxycarbonyl-2-heptylthioethyl]-alanine (α- and β-isomers)

A 3.4 ml quantity of triethylamine was added to a solution of 5.9 g of ethyl ester of S-heptyl-L-cysteine and 5.5 g of t-butyl 2-bromopropionate in 20 ml of HMPA. The mixture was stirred art room temperature for 24 hours. The reaction mixture was poured into ice water and was extracted with ethyl acetate. The extract was sufficiently washed with water and dried over anhydrous sodium sulfate. The solvent was evaporated off under reduced pressure and the residue was separated and purified by silica gel column chromatography (using a 1:3 mixture of ether and n-hexane as an eluent), producing the α-isomer of the title compound from the first eluate as a colorless oil. Yield 2.8 g.

$[\alpha]_D^{20} = +26.9°$ (c=0.9, ethanol).

$^1$H-NMR (CDCl$_3$): δ: 0.88 (3H, t, J=5 Hz), 1.27 (3H, d, J=7 Hz), 1.29 (3H, t, J=7 Hz), 1.4–1.8 (10H, m), 1.45 (9H, s), 2.55 (2H, t, J=7 Hz), 2.80 (2H, d, J=6 Hz), 3.32 (1H, q, J=7 Hz), 3.46 (1H, t, J=7 Hz), 4.20 (2H, q, J=7 Hz).

The β-isomer of the title compound was produced as a colorless oil from the second eluate.

Yield 2.6 g.

$[\alpha]_D^{20} = -38.6°$ (c=1.3, ethanol).

$^1$H-NMR (CDCl$_3$): δ: 0.88 (3H, t, J=7 Hz), 1.29 (3H, t, J=7 Hz), 1.30 (3H, d, J=7 Hz), 1.4–1.8 (10H, m), 1.47 (9H, s), 2.54 (2H, t, J=7 Hz), 2.70 (1H, d-d, J=13 Hz, 7.5 Hz), 2.92 (1H, d-d, J=13 Hz, 5 Hz), 3.29 (1H, q, J=7 Hz), 3.47 (1H, d-d, J=7.5 Hz, 5 Hz), 4.21 (2H, q, J=7 Hz).

REFERENCE EXAMPLES 9–11

The compounds as shown below in Table 3 were prepared by following the general procedure of Reference Example 8.

TABLE 3

$$R_1-S-CH_2\overset{(R)}{\underset{CO_2C_2H_5}{CH}}-NH-\overset{CH_3}{\underset{*}{CH}}-CO_2-C(CH_3)_3$$

| Ref. Ex. No. | $R_1$ | Isomer (*) | Optical Rotation (Solvent: ethanol) | $^1H$—NMR (CDCl$_3$): δ |
|---|---|---|---|---|
| 9 | $CH_3(CH_2)_8$— | α | $[\alpha]_D^{20} = +25.3°$ (c = 0.8) | 0.88 (3H, t, J=5Hz), 1.27 (3H, d, J=7Hz), 1.29 (3H, t, J=7Hz), 1.4–1.8 (14H, m), 1.45 (9H, s), 2.55 (2H, t, J=7Hz), 2.80 (2H, d, J=6Hz), 3.32 (1H, q, J=7Hz), 3.46 (1H, t, J=7Hz), 4.20 (1H, q, J=7Hz) |
| | | β | $[\alpha]_D^{20} = -35.3°$ (c = 0.7) | 0.88 (3H, t, J=5Hz), 1.29 (3H, t, J=7Hz), 1.30 (3H, d, J=7Hz), 1.4–1.8 (14H, m), 1.47 (9H, s), 2.54 (2H, t, J=7Hz), 2.70 (1H, d—d, J=13Hz, 7.5Hz), 2.92 (1H, d—d, J=13Hz, 5Hz), 3.29 (1H, q, J=7Hz), 3.47 (1H, d—d, J=7.5Hz, 5Hz), 4.21 (2H, q, J=7Hz) |
| 10 | $CH_3(CH_2)_{10}$— | α | $[\alpha]_D^{19} = +22.6°$ (c = 1.1) | 0.88 (3H, t, J=5.5Hz), 1.28 (3H, t, J=7Hz), 1.28 (3H, d, J=7Hz), 1.45 (9H, s), 1.2–1.7 (18H, m), 2.13 (1H, br s), 2.54 (2H, t, J=7Hz), 2.80 (2H, d, J=6Hz), 3.31 (1H, q, J=7Hz), 3.46 (1H, t, J=6Hz), 4.20 (2H, q, J=7Hz) |
| | | β | $[\alpha]_D^{19} = -30.9°$ (c = 0.9) | 0.88 (3H, t, J=5.5Hz), 1.29 (3H, t, J=7Hz), 1.29 (3H, d, J=7Hz), 1.46 (9H, s), 1.2–1.7 (18H, m), 2.08 (1H, br s), 2.54 (2H, t, J=7Hz), 2.70 (1H, d—d, J=13.5Hz, 7.5Hz), 2.92 (1H, d—d, J=13.5Hz, 5.5Hz), 3.29 (1H, q, J=7Hz), 3.45 (1H, d—d, J=7.5Hz, 5.5Hz), 4.21 (2H, q, J=7Hz) |
| 11 | cyclohexyl-CH$_2$— | α | $[\alpha]_D^{22} = +29.6°$ (c = 0.7) | 1.27 (3H, d, J=7Hz), 1.29 (3H, t, J=7Hz), 1.45 (9H, s), 0.7–2.0 (11H, m), 2.44 (2H, d, J=6.5Hz), 2.78 (2H, d, J=6Hz), 3.31 (1H, q, J=7Hz), 3.45 (1H, t, J=6Hz), 4.20 (2H, q, J=7Hz) |
| | | β | $[\alpha]_D^{21} = -36.1°$ (c = 0.8) | 1.29 (3H, d, J=7Hz), 1.29 (3H, t, J=7Hz), 1.49 (9H, s), 0.7–2.0 (11H, m), 2.42 (2H, d, J=6.5Hz), 2.70 (1H, d—d, J=13Hz, 7.5Hz), 2.92 (1H, d—d, J=13Hz, 5Hz), 3.29 (1H, q, J=7Hz), 3.47 (1H, d—d, J=7.5Hz, 5Hz), 4.21 (2H, q, J=7Hz) |

REFERENCE EXAMPLE 12

Preparation of N-[(R)-1-ethoxycarbonyl-2-heptylthioethyl]-alanine (α-isomer)

In 10 ml of TFA was dissolved 2.7 g of the α-isomer of t-butyl ester of N-[(R)-1-ethoxycarbonyl-2-heptylthioethyl]-alanine prepared in Reference Example 8. The solution was stirred at room temperature for 3 hours. The TFA was distilled off under reduced pressure. The residue was poured into ice water and the mixture was adjusted to a pH of 4 with a saturated aqueous solution of sodium hydrogencarbonate and extracted with methylene chloride. The extract was washed with water and dried over anhydrous sodium sulfate, and the solvent was evaporated off under reduced pressure. The residue was recrystallized from methylene chloride, giving the α-isomer of the title compound. Yield 2.0 g.

M.p. 130°–132° C.

$[α]_D^{24} = +20.5°$ (c=0.8, DMF).

REFERENCE EXAMPLES 13–19

The compounds as shown below in Table 4 were produced by following the general procedure of Reference Example 12.

TABLE 4

$$R_1-S-CH_2\overset{(R)}{\underset{CO_2C_2H_5}{CH}}-NH-\overset{CH_3}{\underset{*}{CH}}-CO_2H$$

| Ref. Ex. No. | $R_1$ | Isomer (*) | Optical Rotation | Melting point (°C.) |
|---|---|---|---|---|
| 13 | $CH_3(CH_2)_6-$ | β | $[α]_D^{23} = -25.1°$ (c = 0.7, DMF) | 124–126 |
| 14 | $CH_3(CH_2)_8-$ | α | $[α]_D^{24} = +18.3°$ (c = 0.8, DMF) | 128–131 |
| 15 | $CH_3(CH_2)_8-$ | β | $[α]_D^{21} = -22.9°$ (c = 0.7, DMF) | 123–125 |
| 16 | $CH_3(CH_2)_{10}-$ | α | $[α]_D^{22} = +16.7°$ (c = 0.9, DMF) | 124–127 |
| 17 | $CH_3(CH_2)_{10}-$ | β | $[α]_D^{20} = -21.4°$ (c = 0.6, ethanol) | 122–124 |
| 18 | cyclohexyl-$CH_2-$ | α | $[α]_D^{24} = +22.0°$ (c = 0.9, DMF) | 147–150 |
| 19 | cyclohexyl-$CH_2-$ | β | $[α]_D^{22} = -21.7°$ (c = 0.5, DMF) | 139–141 |

REFERENCE EXAMPLE 20

Preparation of
N-[(R)-1-ethoxycarbonyl-2-heptylthioethyl]-(R,S)-alanine

A solution of 5 g of ethyl ester of S-heptyl-L-cysteine hydrochloride in 70 ml of ethanol was mixed with 10 ml of water. To the mixture was added 2.8 g of pyruvic acid with ice cooling. The mixture was adjusted to a pH of 7 with a 4N solution of sodium hydroxide. A 2.3 g quantity of sodium cyanoborohydride was gradually added to the mixture and the resulting mixture was stirred at room temperature for 15 hours. The solvent was distilled off under reduced pressure. The residue was dissolved in a saturated aqueous solution of sodium hydrogencarbonate to obtain a weakly alkaline solution. The solution was washed with ether. The aqueous layer was adjusted to a pH of 4 with a 1N solution of hydrochloric acid and was extracted with ethyl acetate. The extract was washed with water and dried over anhydrous sodium sulfate, and the solvent was evaporated off under reduced pressure, giving 3.9 g of the title compound.

EXAMPLE 13

Preparation of t-butyl ester of
N-[(R)-1-ethoxycarbonyl-2-heptylthioethyl]-alanyl-(S)-proline (β-isomer)

A solution of 590 mg of DEPC (90% content) in 2 ml of DMF was added with ice cooling and stirring to a solution of 1.0 g of the N-[(R)-1-ethoxycarbonyl-2-heptylthioethyl]-alanine (β-isomer) obtained in Reference Example 13 and 580 mg of t-butyl ester of (S)-proline in 14 ml of DMF. To the mixture was gradually added dropwise a solution of 1.43 ml of triethylamine in 2 ml of DMF. The resulting mixture was stirred with ice cooling for 2 hours and further stirred at room temperature for 10 hours. The reaction mixture was poured into ice water. A saturated aqueous solution of sodium hydrogencarbonate was added to the mixture to give a weakly alkaline solution. The mixture was extracted with ethyl acetate. The extract was sufficiently washed with water and dried over anhydrous sodium sulfate. The solvent was evaporated off under reduced pressure. The residue was purified by silica gel column chromatography (using a 30:1 mixture of chloroform and methanol as an eluent), giving the title compound as a colorless oil. Yield 1.4 g.

$[α]_D^{22} = -92.0°$ (c=0.7, ethanol).

$^1$H-NMR (CDCl$_3$): δ: 0.88 (3H, t, J=5 Hz), 1.29 (3H, t, J=7 Hz), 1.29 (3H, d, J=6.5 Hz), 1.2–1.8 (10H, m), 1.44, 1.46 (total 9H, each s), 1.8–2.3 (4H, m), 2.52 (2H, t, J=7 Hz), 2.69 (1H, d-d, J=13 Hz, 7.5 Hz), 2.91 (1H, d-d, J=13 Hz, 6 Hz), 3.2–3.7 (4H, m), 4.20 (2H, q, J=7 Hz), 4.3–4.5 (1H, m).

EXAMPLES 14–16

The compounds as shown below in Table 5 were prepared by following the general procedure of Example 13.

TABLE 5

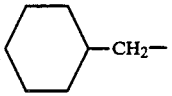

| Example No. | $R_1$ | Isomer (*) | Optical Rotation (Solvent: ethanol) | $^1$H—NMR (CDCl$_3$): δ |
|---|---|---|---|---|
| 14 | CH$_3$(CH$_2$)$_8$— | β | $[\alpha]_D^{21} = -87.8°$ (c = 0.7) | 0.88 (3H, t, J=5Hz), 1.29 (3H, t, J=7Hz), 1.30 (3H, d, J=7Hz), 1.2–1.8 (14H, m), 1.44, 1.47 (total 9H, each s), 1.8–2.3 (4H, m), 2.52 (2H, t, J=7Hz), 2.69 (1H, d—d, J=13Hz, 7.5Hz), 2.91 (1H, d—d, J=13Hz, 6Hz), 3.2–3.7 (4H, m), 4.20 (2H, q, J=7Hz), 4.3–4.5 (1H, m) |
| 15 | CH$_3$(CH$_2$)$_{10}$— | β | $[\alpha]_D^{20} = -78.0°$ (c = 0.8) | 0.88 (3H, t, J=5.5Hz), 1.29 (3H, t, J=7Hz), 1.29 (3H, d, J=7Hz), 1.44, 1.46 (total 9H, each s), 1.2–1.7 (18H, m), 1.7–2.3 (4H, m), 2.54 (2H, t, J=7Hz), 2.65 (1H, d—d, J=13.5Hz, 7.5Hz), 2.93 (1H, d—d, J=13.5Hz, 5.5Hz), 3.2–3.7 (4H, m), 4.20 (2H, q, J=7Hz), 4.4–4.5 (1H, m) |
| 16 | cyclohexyl-CH$_2$— | β | $[\alpha]_D^{21} = -81.8°$ (c = 1.0) | 1.29 (3H, t, J=7Hz), 1.29 (3H, d, J=7Hz), 1.44, 1.46 (total 9H, each s), 0.7–2.2 (15H, m), 2.41 (2H, d, J=7Hz), 2.70 (1H, d—d, J=13Hz, 7.5Hz), 2.92 (1H, d—d, J=13Hz, 5Hz), 3.2–3.6 (4H, m), 4.20 (2H, q, J=7Hz), 4.3–4.5 (1H, m) |

EXAMPLE 17

Preparation of N-[(R)-1-ethoxycarbonyl-2-heptylthioethyl]-alanyl-(S)-proline (β-isomer) and L-arginine salt thereof In 5 ml of TFA were dissolved 750 mg of the t-butyl ester of N-[(R)-1-ethoxycarbonyl-2-heptylthioethyl]-alanyl-(S)-proline (β-isomer) prepared in Example 13 and 0.52 ml of anisole. The solution was stirred at room temperature for 2.5 hours. The TFA was distilled off under reduced pressure and the residue was dissolved in a saturated aqueous solution of hydrogencarbonate to adjust its pH to 8. The solution was washed with ether and the aqueous layer was adjusted to a pH of 4 with a 1N solution of hydrochloric acid and extracted with methylene chloride. The extract was washed with water and dried over anhydrous sodium sulfate and the solvent was evaporated off under reduced pressure, giving the β-isomer of the title compound as a colorless oil. Yield 580 mg.

A 550 mg quantity of the the compound obtained above was dissolved in 10 ml of ethanol. To the solution was added a solution of 230 mg of L-arginine in 4 ml of water. The solvent was distiled off under reduced pressure. Ethanol was added to the residue and distilled off under reduced pressure and this procedure was repeated several times. The residue was reprecipitated with ethanol-ether, affording 650 mg of L-arginine salt of the title compound.

M.p. 64°–68° C.
$[\alpha]_D^{24} = -57.3°$ (c=0.8, ethanol).

EXAMPLE 18

Preparation of N-[(R)-1-ethoxycarbonyl-2-heptylthioethyl]-alanyl-(S)-proline (β-isomer) and maleate In 10 ml of ether was dissolved 720 mg of the N-[(R)-1-ethoxycarbonyl-2-heptylthioethyl]-alanyl-(S)-proline (β-isomer) obtained in Example 17. To the solution was added with ice cooling a solution of 200 mg of maleic acid in 15 ml of ethyl acetate. The precipitated crystals were filtered and the crystals were recrystallized from ethyl acetate-ether, giving 670 mg of the title compound.

M.p. 76°–79° C.
$[\alpha]_D^{25} = -62.3°$ (c=0.7, ethanol).

EXAMPLES 19-21

The general procedure of Example 17 was followed, thereby producing the compounds as shown below in Table 6.

TABLE 6

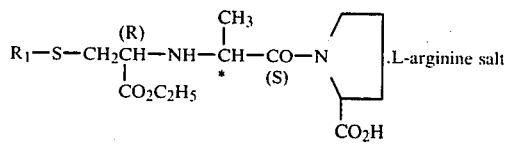

1.8–2.3 (4H, m), 2.3–2.9 (4H, m), 3.3–3.8 (4H, m), 4.0–4.5 (3H, m).

EXAMPLES 23–27

The compounds as shown below in Table 7 were prepared by following the general procedure of Example 22.

TABLE 7

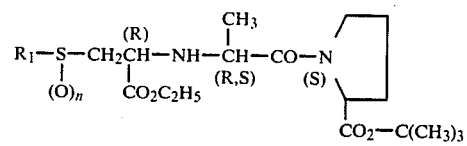

| Example No. | $R_1$ | n | Optical Rotation (Solvent: ethanol) | $^1$H—NMR (CDCl$_3$):δ |
|---|---|---|---|---|
| 23 | CH$_3$(CH$_2$)$_8$— | 0 | $[\alpha]_D^{20} = -48.9°$ (c=0.9) | 0.88 (3H, t, J=5Hz), 1.2–1.7 (20H, H, m), 1.44, 1.46 (total 9H, each s), 1.8–2.7 (6H, m), 2.7–2.9 (2H, m), 3.2–3.9 (4H, m), 4.0–4.5 (3H, m) |
| 24 | CH$_3$(CH$_2$)$_5$— | 2 | $[\alpha]_D^{21} = -45.8°$ (c=0.8) | 0.89 (3H, t, J=5Hz), 1.2–1.4 (6H, m), 1.45, 1.47 (total 9H, each s), 1.2–2.4 (12H, m), 3.1–3.4 (4H, m), 3.4–4.0 (4H, m), 4.1–4.5 (3H, m) |
| 25 | cyclohexyl-CH$_2$— | 0 | $[\alpha]_D^{21} = -43.3°$ (c=0.8) | 1.2–1.4 (6H, m), 1.45, 1.46 (total 9H, each s), 0.7–2.2 (15H, m), 2.3–2.5 (2H, m), 2.6–2.9 (2H, m), 3.2–3.8 (4H, m), 4.0–4.5 (3H, m) |
| 26 | (CH$_3$)$_2$C=CH—CH$_2$— | 0 | $[\alpha]_D^{20} = -70.3°$ (c=0.9) | 1.2–1.4 (6H, m), 1.44, 1.45 (total 9H, each s), 1.67 (3H, s), 1.73 (3H, s), 1.8–2.3 (4H, m), 2.6–2.9 (2H, m), 3.1–3.3 (2H, m), 3.3–3.9 (4H, m), 4.0–4.5 (3H, m), 5.21 (1H, t, J=8Hz) |
| 27 | CH$_3$(CH$_2$)$_5$— | 1 | $[\alpha]_D^{21} = -55.1°$ (c=0.8) | 0.89 (3H, t, J=5Hz), 1.2–1.7 (6H, m), 1.44, 1.47 (total 9H, each s), 1.3–2.4 (12H, m), 2.5–3.2 (4H, m), 3.3–3.9 (4H, m), 4.0–4.5 (3H, m) |

| Example No. | $R_1$ | Isomer (*) | Optical Rotation (Solvent: ethanol) | Melting point (°C.) |
|---|---|---|---|---|
| 19 | CH$_3$(CH$_2$)$_8$ | β | $[\alpha]_D^{20} = -53.0°$ (c=0.7) | 82–87 |
| 20 | CH$_3$(CH$_2$)$_{10}$— | β | $[\alpha]_D^{19} = -52.7°$ (c=1.0) | 45–50 |
| 21 | cyclohexyl-CH$_2$— | β | $[\alpha]_D^{20} = -54.3°$ (c=0.7) | 83–89 |

EXAMPLE 22

Preparation of t-butyl ester of N-[(R)-1-ethoxycarbonyl-2-heptylthioethyl]-(R,S)-alanyl-(S)-proline The title compound was prepared as a colorless oil from 1.0 g of the N-[(R)-1-ethoxycarbonyl-2-heptylthioethyl]-(R,S)-alanine prepared in Reference Example 20 by following the general procedure of Example 13. Yield 1.3 g.

$[\alpha]_D^{21} = -54.3°$ (c=0.8, ethanol).

$^1$H-NMR (CDCl$_3$): δ: 0.88 (3H, t, J=5 Hz), 1.2–1.4 (6H, m), 1.44, 1.46 (total 9H, each s), 1.2–1.8 (10H, m),

EXAMPLE 28

Preparation of N-[(R)-1-ethoxycarbonyl-2-heptylthioethyl]-(R,S)-alanyl-(S)-proline and L-arginine salt thereof In 4 ml of TFA were dissolved 530 mg of the t-butyl ester of N-[(R)-1-ethoxycarbonyl-2-heptylthioethyl]-(R,S)-alanyl-(S)-proline prepared in Example 22 and 0.4 ml of anisole. The mixture was stirred at room temperature for 2.5 hours. The TFA was distilled off under reduced pressure. The residue was dissolved in a saturated aqueous solution of sodium hydrogencarbonate to adjust its pH to 8. The solution was washed with ether and the aqueous layer was adjusted to a pH of 4 with a 1N solution of hydrochloric acid and extracted with methylene chloride. The extract was washed with water and dried over anhydrous sodium sulfate, and the solvent was evaporated off under reduced pressure, giving the title compound as a colorless oil. Yield 370 mg.

A 330 mg quantity of the compound obtained above was dissolved in 8 ml of ethanol. To the solution was added a solution of 137 mg of L-arginine in 3 ml of water. The solvent was distilled off under reduced pressure. Ethanol was added to the residue and distilled off under reduced pressure and the procedure was several times repeated. Anhydrous ether was added to the residue and the precipitated crystals were filtered, giving the L-arginine salt of the title compound. Yield 370 mg.

M.p. 55°–64° C.

$[\alpha]_D^{20} = -40.3°$ (c=0.7, ethanol).

EXAMPLES 29–33

The compounds as shown below in Table 8 were prepared by following the general procedure of Example 28.

TABLE 8

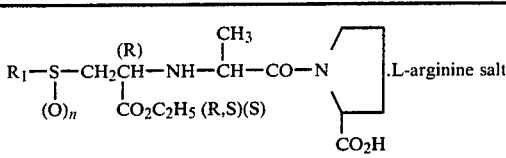

| Example No. | $R_1$ | n | Optical Rotation (Solvent: ethanol) | Melting point (°C.) |
|---|---|---|---|---|
| 29 | $CH_3(CH_2)_8$— | 0 | $[\alpha]_D^{19} = -35.6°$ (c=0.7) | 75–82 |
| 30 | $CH_3(CH_2)_5$— | 2 | $[\alpha]_D^{21} = -26.3°$ (c=0.8) | 70–74 |
| 31 | ⌬—CH₂— | 0 | $[\alpha]_D^{21} = -31.7°$ (c=0.7) | 56–62 |
| 32 | (CH₃)₂C=CH—CH₂— | 0 | $[\alpha]_D^{21} = -44.0°$ (c=0.8) | 67–77 |
| 33 | $CH_3(CH_2)_5$— | 1 | $[\alpha]_D^{22} = -26.7°$ (c=0.7) | 72–78 |

EXAMPLE 34

Preparation of N-[(R)-1-carboxy-2-heptylthioethyl]-alanyl-(S)-proline (β-isomer)

A 2.0 ml quantity of a 1N aqueus solution of sodium hydroxide was added with ice cooling and stirring to a solution of 373 mg of the N-[(R)-1-ethoxycarbonyl-2-heptylthioethyl]-alanyl-(S)-proline (β-isomer) prepared in Example 17 in 4 ml of ethanol. The mixture was stirred at room temperature for 3 hours and applied to a column (Dowex 50W-X8(H+)). The reaction product was sufficiently washed with water and was eluted with a 4% aqueous solution of pyridine. Fractions of the title compound were collected and lyophilized. The powdery substance thus obtained was reprecipitated with ethanol-ether, giving the title compound.

Yield 240 mg.

M.p. 75°–83° C.

$[\alpha]_D^{23} = -108.1°$ (c=0.6, ethanol).

EXAMPLES 35–38

The compounds as shown below in Table 9 were prepared by following the general procedure of Example 34.

TABLE 9

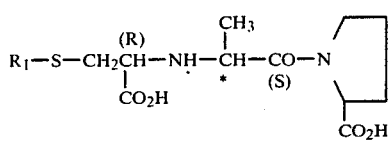

| Example No. | $R_1$ | Isomer (*) | Optical Rotation (Solvent: ethanol) | Melting point (°C.) |
|---|---|---|---|---|
| 35 | $CH_3(CH_2)_8$— | β | $[\alpha]_D^{22} = -95.3°$ (c=0.7) | 69–77 |
| 36 | $CH_3(CH_2)_{10}$— | β | $[\alpha]_D^{22} = -74.2°$ (c=0.3) | 77–84 |
| 37 | $CH_3(CH_2)_8$— | RS | $[\alpha]_D^{19} = -66.0°$ (c=0.6) | 75–86 |
| 38 | ⌬—CH₂— | β | $[\alpha]_D^{24} = -105.3°$ (c=0.4) | 86–91 |

EXAMPLES 39–42

The compounds as shown below in Table 10 were prepared by following the general procedure of Example 13.

TABLE 10

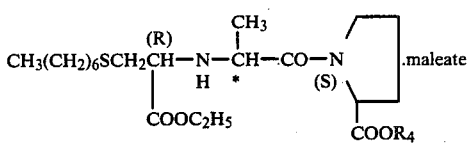

| Example No. | $R_4$ | Isomer (*) | Optical Rotation (Solvent: $C_2H_5OH$) | Melting point (°C.) |
|---|---|---|---|---|
| 39 | $CH_3$ | β | $[\alpha]_D^{23} = -70.3°$ (c=0.7) | 82–84 |
| 40 | $C_2H_5$ | β | $[\alpha]_D^{15} = -68.3°$ (c=1.0) | 82–86 |
| 41 | —C(CH₃)₃ | β | $[\alpha]_D^{17} = -62.4°$ (c=1.0) | 72–75 |
| 42 | —CH₂—⌬ | β | $[\alpha]_D^{18} = -70.4°$ (c=0.7) | 109–111 |

EXAMPLES 43 AND 44

The compounds as shown below in Table 11 were prepared by following the general procedure of Example 17.

TABLE 11

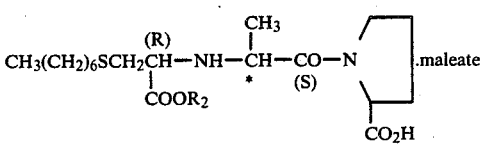

| Example No. | $R_2$ | Isomer (*) | Optical Rotation (Solvent: ethanol) | Melting point (°C.) |
|---|---|---|---|---|
| 43 | —CH(CH₃)₂ | β | $[\alpha]_D^{18} = -60.8°$ (c=0.5) | 103–104 |
| 44 | —CH₂CH(CH₃)₂ | β | $[\alpha]_D^{18} = -60.7°$ (c=0.6) | 110–111 |

REFERENCE EXAMPLE 21

Preparation of t-butyl ester of N-[(R)-1-ethoxycarbonyl-2-ethoxycarbonylmethylthioethyl]-alanine (A- and B-isomers)

In 10 ml of HMPA were dissolved 5.3 g of ethyl ester of S-ethoxycarbonylmethyl-L-cysteine and 4.7 g of t-butyl 2-bromopropionate. A 2.3 g quantity of triethylamine was added to the solution and the mixture was stirred at room temperature for 62 hours. Ice water was added to the reaction mixture and the resulting mixture was extracted with ethyl acetate. The extract was washed sequentially with water and with a saturated aqueous solution of sodium chloride and dried over anhydrous sodium sulfate. The extract was distilled under reduced pressure. The residue was separated and purified by silica gel column chromatography (using a 5:3 mixture of ether and n-hexane as an eluent), producing the A-isomer of the title compound as a colorless oil from the first eluate. Yield 2.1 g.

$[\alpha]_D^{20} = +26.9°$ (c=1.1, methanol).

$^1$H-NMR (CDCl$_3$): δ: 1.27 (3H, d, J=7 Hz), 1.29 (6H, t, J=7 Hz), 1.44 (9H, s), 2.15 (1H, br s), 2.94 (2H, d, J=5 Hz), 3.30 (1H, q, J=7 Hz), 3.33 (2H, s), 3.53 (1H, t, J=5 Hz), 4.19 (2H, q, J=7 Hz), 4.20 (2H, q, J=7 Hz).

The B-isomer of the title compound was prepared as a colorless oil from the second eluate.

Yield 2.24 g.

$[\alpha]_D^{20} = -43.1°$ (c=1.1, methanol).

$^1$H-NMR (CDCl$_3$): δ: 1.29 (3H, d, J=7 Hz), 1.29 (6H, t, J=7 Hz), 1.46 (9H, s), 2.0 (1H, br s), 2.82 (1H, d-d, J=13 Hz, 7 Hz), 3.05 (1H, d-d, J=13 Hz, 6 Hz), 3.30 (1H, q, J=7 Hz), 3.31 (2H, s), 3.57 (1H, d-d, J=7 Hz, 6 Hz), 4.19 (2H, q, J=7 Hz), 4.21 (2H, q, J=7 Hz).

REFERENCE EXAMPLE 22

Preparation of N-[(R)-1-ethoxycarbonyl-2-ethoxycarbonylmethylthioethyl]-alanine (A-isomer)

A 0.93 g quantity of anisole was added to a solution of 1.04 g of the A-isomer of the t-butyl ester of N-[(R)-1-ethoxycarbonyl-2-ethoxycarbonylmethylthioethyl]-alanine obtained in Reference Example 21 in 5 ml of trifluoroacetic acid (TFA). The mixture was stirred at room temperature for 2 hours. The TFA was distilled off under reduced pressure. The residue was adjusted to a pH of 8 with a saturated aqueous solution of sodium hydrogencarbonate and the mixture was washed with ether. Citric acid was added to the aqueous layer to adjust its pH to 4. The mixture was extracted with methylene chloride, the extract was dried over anhydrous sodium sulfate and the solvent was evaporated off under reduced pressure, giving the A-isomer of the title compound as an amophous substance. Yield 0.50 g.

$[\alpha]_D^{20} = +17.3°$ (c=1.0, methanol).

$^1$H-NMR (CDCl$_3$): δ: 1.29 (6H, t, J=7 Hz), 1.43 (3H, d, J=7 Hz), 2.90 (1H, d-d, J=13 Hz, 7H), 3.16 (1H, d-d, J=13 Hz, 6 Hz), 3.30 (2H, s), 3.44 (1H, q, J=7 Hz), 3.65 (1H, d-d, J=7 Hz, 6 Hz), 4.20 (2H, q, J=7 Hz), 4.23 (2H, q, J=7 Hz).

REFERENCE EXAMPLE 23

Preparation of N-[(R)-1-ethoxycarbonyl-2-ethoxycarbonylmethylthioethyl]-alanine (B-isomer)

A 0.97 g quantity of anisole was added to a solution of 1.09 g of the B-isomer of the t-butyl ester of N-[(R)-1-ethoxycarbonyl-2-ethoxycarbonylmethylthioethyl]-alanine obtained in Reference Example 21 in 5 ml of TFA. The B-isomer of the title compound was produced as an amorphous substance by subjecting the mixture to the same reaction and treatment as in Reference Example 22. Yield 0.43 g.

$[\alpha]_D^{20} = -32.0°$ (c=0.8, methanol).

$^1$H-NMR (CDCl$_3$): δ: 1.29, 1.30 (6H, t, J=7 Hz), 1.46 (3H, d, J=7 Hz), 2.79 (1H, d-d, J=13 Hz, 9 Hz), 3.12 (1H, d-d, J=13 Hz, 5 Hz), 3.27 (2H, s), 3.35 (1H, q, J=7 Hz), 3.48 (1H, d-d, J=9 Hz, 5 Hz), 4.20 (2H, q, J=7 Hz), 4.21 (2H, q, J=7 Hz).

EXAMPLE 45

Preparation of t-butyl ester of N-[(R)-1-ethoxycarbonyl-2-ethoxycarbonylmethylthioethyl]-alanyl-(S)-proline (A-isomer)

A solution of 188 mg of triethylamine in 3 ml of DMF was gradually added dropwise with ice cooling and stirring to a solution of 520 mg of the A-isomer of the N-[(R)-1-ethoxycarbonyl-2-ethoxycarbonylmethylthioethyl]-alanine obtained in Reference Example 22, 319 mg of t-butyl ester of (S)-proline and 304 mg of DEPC in 5 ml of DMF. The mixture was stirred for 12 hours while being allowed to slowly come to room temperature. Ice water was added to the reaction mixture and the mixture was made weakly alkaline with a saturated aqueous solution of sodium hydrogencarbonate. The mixture was extracted with ethyl acetate. The extract was washed sequentially with water and with a saturated aqueous solution of sodium chloride and dried over anhydrous sodium sulfate. Then the extract was distilled under reduced pressure. The residue was purified by silica gel column chromatography (using a 10:1 mixture of chloroform and methanol as an eluent), giving the A-isomer of the title compound as a colorless oil. Yield 400 mg.

$[\alpha]_D^{20} = -46.2°$ (c=1.0, methanol).

$^1$H-NMR (CDCl$_3$): δ: 1.29 (3H, t, J=7 Hz), 1.33 (3H, t, J=7 Hz) 1.3–1.5 (3H, m), 1.44, 1.46 (total 9H, each s), 1.8–3.8 (13H, m), 4.08 (4H, q, J=7 Hz).

EXAMPLE 46

Preparation of t-butyl ester of N-[(R)-1-ethoxycarbonyl-2-ethoxycarbonylmethylthioethyl]-alanyl-(S)-proline (B-isomer)

The general procedure of Example 45 was followed using 450 mg of the B-isomer of the N-[(R)-1-ethoxycarbonyl-2-ethoxycarbonylmethylthioethyl]-alanine prepared in Reference Example 23, thereby producing 560 mg of the B-isomer of the title compound as a colorless oil.

$[\alpha]_D^{20} = -93.6°$ (c=1.0, methanol).

$^1$H-NMR (CDCl$_3$): δ: 1.29 (3H, t, J=7 Hz), 1.33 (3H, t, J=7 Hz), 1.3–1.5 (3H, m), 1.44, 1.46 (total 9H, each s), 1.8–3.8 (13H, m), 4.08 (4H, q, J=7 Hz).

EXAMPLE 47

Preparation of N-[(R)-1-ethoxycarbonyl-2-ethoxycarbonylmethylthioethyl]-alanyl-(S)-proline (A-isomer) and maleate thereof A 240 mg quantity of anisole was added to a solution of 340 mg of the A-isomer of t-butyl ester of N-[(R)-1-ethoxycarbonyl-2-ethoxycarbonylmethylthioethyl]-alanyl-(S)-proline prepared in Example 45 in 3 ml of TFA.

The same subsequent reaction and treatment as in Reference Example 22 were conducted, thereby producing the A-isomer of the title compound as a colorless oil. Yield 80 mg.

A solution of 23 mg of maleic acid in 3 ml of ether was added with stirring to a solution of 80 mg of the A-isomer obtained by the foregoing reaction. The solids were precipitated and the precipitate was filtered and dried, affording the maleate of the title compound. Yield 30 mg.

$[\alpha]_D^{20} = -3.2°$ (c=0.4, methanol).

$^1$H-NMR (CD$_3$OD): δ: 1.28 (3H, t, J=7 Hz), 1.33 (3H, t, J=7 Hz), 1.57 (3H, t, J=7 Hz), 1.9–2.3 (4H, m), 3.1–3.9 (5H, m), 3.46 (2H, s), 4.19 (2H, q, J=7 Hz), 4.32 (1H, q, J=7 Hz), 4.3–4.5 (1H, m), 6.29 (2H, s).

EXAMPLE 48

Preparation of N-[(R)-1-ethoxycarbonyl-2-ethoxycarbonylmethylthioethyl]-alanyl-(S)-proline (B-isomer) and maleate thereof By following the general procedure of Reference Example 22, the B-isomer of the title compound was prepared as a colorless oil from 520 mg of the B-isomer of t-butyl ester of N-[(R)-1-ethoxycarbonyl-2-ethoxycarbonylmethylthioethyl]-alanyl-(S)-proline obtained in Example 46. Yield 340 mg.

The general procedure of Example 47 was carried out using 340 mg of the B-isomer obtained by the foregoing reaction, thereby giving the maleate of the title compound. Yield 320 mg.

$[\alpha]_D^{21} = -54.6°$ (c=0.9, methanol).

$^1$H-NMR (CD$_3$OD): δ: 1.28 (3H, t, J=7 Hz), 1.33 (3H, t, J=7 Hz), 1.61 (3H, d, J=7 Hz), 1.9–2.4 (4H, m), 3.2–3.8 (5H, m), 3.42 (2H, s), 4.20 (4H, q, J=7 Hz), 4.32 (1H, q, J=7 Hz), 4.3–4.5 (1H, m), 6.29 (2H, s).

REFERENCE EXAMPLE 24

Preparation of N-[(R)-1-ethoxycarbonyl-2-[(R,S)-1-ethoxycarbonylhexylthio]ethyl]-(R,S)-alanine A solution of 7.7 g of ethyl ester of S-[(R,S)-1-ethoxycarbonylhexyl]-L-cysteine in 25 ml of ethanol was mixed with 10 ml of water. To the mixture was added 11.1 g of pyruvic acid. The resulting mixture was neutralized with a 4N aqueous solution of sodium hydroxide. A 3.2 g quantity of sodium cyanoborohydride was gradually added thereto with ice cooling and stirring and reaction was conducted at room temperature for 14 hours. After the completion of the reaction, the ethanol was distilled off and the reaction mixture was rendered weakly alkaline with a saturated aqueous solution of sodium hydrogencarbonate. The solution was washed with ether and the aqueous layer was separated. The aqueous layer was adjusted to a pH of 4 with a 10% solution of hydrochloric acid and the mixture was extracted with ethyl acetate. The extract was washed sequentially with water and with a saturated aqueous solution of sodium chloride and dried over anhydrous sodium sulfate. The extract was distilled under reduced pressure and the residue was purified by silica gel column chromatography (using a 10:1 mixture of chloroform and methanol as an eluent), giving the title compound as a colorless amorphous substance. Yield 7.0 g.

$[\alpha]_D^{20} = -7.4°$ (c=1.1, ethanol).

$^1$H-NMR (CDCl$_3$): δ: 0.89 (3H, t, J=5 Hz), 1.29 (6H, t, J=7 Hz), 1.39 (3H, d, J=7 Hz), 1.3–2.1 (8H, m), 2.7–3.8 (5H, m), 4.21 (2H, q, J=7 Hz), 4.22 (2 H, q, J=7 Hz).

REFERENCE EXAMPLES 25-28

The compounds as shown below in Table 12 were prepared by following the general procedure of Reference Example 24.

TABLE 12

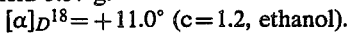

| Ref. Ex. No. | R$_5$ | Optical Rotation | $^1$H—NMR (CDCl$_3$):δ |
|---|---|---|---|
| 25 | —CH$_3$ | $[\alpha]_D^{23} = -9.3°$ (c=0.9, methanol) | 1.29 (6H, t, J=7Hz), 1.42 (3H, d, J=7Hz), 1.44 (3H, d, J=7Hz), 2.7–3.2 (2H, m), 3.3–3.7 (3H, m), 4.19 (2H, q, J=7Hz), 4.21 (2H, q, J=7Hz) |
| 26 | —CH$_2$(CH$_2$)$_2$CH$_3$ | $[\alpha]_D^{24} = +38.8°$ (c=0.8, ethanol) | 0.90 (3H, t, J=5Hz), 1.2–1.5 (9H, m), 1.3–2.1 (6H, m), 2.8–3.1 (2H, m), 3.2–3.7 (3H, m), 4.21 (2H, q, J=7Hz), 4.23 (2H, q, J=7Hz) |
| 27 | —CH$_2$CH(CH$_3$)$_2$ | $[\alpha]_D^{18} = +0.45°$ (c=1.1, ethanol) | 0.92 (6H, d, J=4.5Hz), 1.30 (6H, t, J=7Hz), 1.3–1.9 (6H, m), 2.8–3.8 (5H, m), 4.20 (2H, q, J=7Hz), 4.23 (2H, q, J=7Hz) |
| 28 | (phenyl) | $[\alpha]_D^{24} = -4.0°$ (c=0.8, ethanol) | 1.1–1.5 (9H, m), 2.6–3.0 (2H, m), 3.1–3.6 (2H, m), 4.16 (2H, q, J=7Hz), 4.19 (2H, q, J=7Hz), 4.66, 4.73 (1H, each s), 7.2–7.6 (5H, m) |

REFERENCE EXAMPLE 29

Preparation of N-[(R)-1-ethoxycarbonyl-2-[(R,S)-1-t-butoxycarbonylhexylthio]ethyl]-(R,S)-alanine The title compound was produced as a colorless amorphous substance from 5.5 g of ethyl ester of S-[(R,S)-1-t-butoxycarbonylhexyl]-L-cysteine by following the general procedure of Reference Example 24. Yield 5.37 g.

$[\alpha]_D^{18} = +11.0°$ (c=1.2, ethanol).

$^1$H-NMR (CDCl$_3$): δ: 0.89 (3H, t, J=5 Hz), 1.29 (3H, t, J=7 Hz), 1.48 (9H, s), 1.3–2.0 (11H, m), 2.8–3.8 (5H, m), 4.22 (2H, q, J=7 Hz).

EXAMPLE 49

Preparation of t-butyl ester of N-[(R)-1-ethoxycarbonyl-2-[(R,S)-1-ethoxycarbonylhexylthio]ethyl]-(R,S)-alanyl-(S)-proline The title compound was prepared as a colorless oil from 2.0 g of the N-[(R)-1-ethoxycarbonyl-2-[(R,S)-1-ethoxycarbonylhexylthio]ethyl]-(R,S)-alanine obtained in Reference Example 24 by following the general procedure of Example 45. Yield 2.8 g.

$[\alpha]_D^{19} = -46.2°$ (c=0.9, ethanol).

$^1$H-NMR (CDCl$_3$): δ: 0.88 (3H, t, J=5 Hz), 1.28 (6H, t, J=7 Hz), 1.3-1.5 (3H, m), 1.44, 1.46 (total 9H, each s), 1.5-2.3 (12H, m), 2.8-3.0 (2H, m), 3.1-3.8 (6H, m), 4.19 (4H, q, J=7 Hz).

EXAMPLES 50-53

The general procedure of Example 49 was followed, thereby producing the compounds as shown below in Table 13.

TABLE 13

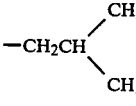

| Example No. | R$_5$ | Optical Rotation | $^1$H—NMR (CDCl$_3$):δ |
|---|---|---|---|
| 50 | —CH$_3$ | $[\alpha]_D^{23}$ = −30.2° (c=0.9, methanol) | 1.29 (6H, t, J=7Hz), 1.44, 1.46 (total 9H, each s), 1.3-1.5 (6H, m), 1.8-2.3 (4H, m), 2.8-3.1 (2H, m), 3.3-3.8 (6H, m), 4.19 (2H, q, J=7Hz) |
| 51 | —CH$_2$(CH$_2$)$_2$CH$_3$ | $[\alpha]_D^{23}$ = −10.6° (c=0.8, ethanol) | 0.89 (3H, t, J=5Hz), 1.2-1.4 (9H, m), 1.44, 1.46 (total 9H, each s), 1.5-2.5 (10H, m), 2.7-3.1 (2H, m), 3.1-3.9 (6H, m), 4.19 (4H, q, J=7Hz) |
| 52 | —CH$_2$CH(CH$_3$)$_2$ | $[\alpha]_D^{20}$ = −39.3° (c=1.0, ethanol) | 0.90 (6H, d, J=5Hz), 1.28 (6H, t, J=7Hz), 1.44, 1.46 (total 9H, each s), 1.3-1.5 (3H, m), 1.5-3.1 (10H, m), 3.3-3.8 (6H, m), 4.19 (4H, q, J=7Hz) |
| 53 |  | $[\alpha]_D^{25}$ = −39.2° (c=0.8, ethanol) | 1.1-1.4 (9H, m), 1.44, 1.45 (total 9H, each s), 1.6-2.5 (4H, m), 2.6-3.0 (2H, m), 3.2-3.8 (3H, m), 4.18 (4H, q, J=7Hz), 7.2-7.6 (5H, m) |

EXAMPLE 54

Preparation of t-butyl ester of N-[(R)-1-ethoxycarbonyl-2-[(R,S)-1-t-butoxycarbonyl-hexylthio]ethyl]-(R,S)-alanyl-(S)-proline The same reaction and treatment as in Example 45 were repeated using 1.0 g of the N-[(R)-1-ethoxycarbonyl-2-[(R,S)-1-t-butoxycarbonylhexylthio]ethyl]-(R,S)-alanine obtained in Reference Example 29 and the resulting residue was purified by silica gel column chromatography (using a 20:1 mixture of chloroform and methanol as an eluent), giving the title compound as a colorless oil. Yield 1.03 g.

$[\alpha]_D^{19}$ = −26.2° (c=0.9, ethanol).

$^1$H-NMR (CDCl$_3$): δ: 0.88 (3H, t, J=5 Hz), 1.28 (3H, t, J=7 Hz), 1.44, 1.47 (total 9H, each s), 1.48 (9H, s), 1.3-2.4 (15H, m), 2.8-3.0 (2H, m), 3.1-3.8 (6H, m), 4.19 (2H, q, J=7 Hz).

EXAMPLE 55

Preparation of N-[(R)-1-ethoxycarbonyl-2-[(R,S)-1-ethoxycarbonyl-hexylthio]ethyl]-(R,S)-alanyl-(S)-proline and L-arginine salt thereof The procedure of Reference Example 22 was followed using 407 mg of the t-butyl ester of N-[(R)-1-ethoxycarbonyl-2-[(R,S)-1-ethoxycarbonylhexylthio]-ethyl]-(R,S)-alanyl-(S)-proline obtained in Example 49, thereby giving the title compound as a colorless amorphous substance. Yield 110 mg.

A solution of 110 mg of L-arginine in 1.5 ml of water was added with stirring to a solution of 300 mg of the compound obtained by the foregoing reaction in 5 ml of ethanol. The water and ethanol was distilled off, and dried under reduced pressure, giving the L-arginine salt of the title compound as a colorless powder. Yield 342 mg.

Colorless crystal, M.p. 50°-55° C.

$[\alpha]_D^{20}$ = −33.0° (c=0.96, ethanol)

EXAMPLES 56-59

The general procedure of Example 55 was followed, producing the compounds as shown below in Table 14.

TABLE 14

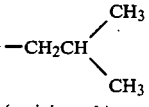

| Example No. | R$_5$ | Optical Rotation | $^1$H—NMR (CDCl$_3$):δ |
|---|---|---|---|
| 56 | —CH$_3$ | $[\alpha]_D^{21}$ = −10.5° (c=0.9, methanol) (maleate) | 1.29 (6H, t, J=7Hz), 1.4-1.7 (6H, m), 1.9-2.4 (4H, m), 3.3-3.9 (8H, m), 4.21 (4H, q, J=7Hz), 6.30 (2H, s) |
| 57 | —CH$_2$(CH$_2$)$_2$CH$_3$ (maleate) | $[\alpha]_D^{23}$ = −2.9° (c=0.6, ethanol) | 0.90 (3H, t, J=5Hz), 1.1-1.6 (9H, m), 1.6-2.5 (10H, m), 3.1-3.8 (7H, m), 4.20 (4H, q, J=7Hz), 6.27 (2H, s) |
| 58 | —CH$_2$CH(CH$_3$)$_2$ (arginine salt) | $[\alpha]_D^{18}$ = −30.7° (c=0.8, ethanol) | mp. 78-86° C. (arginine salt) $^1$H—NMR (free compound) 0.91 (6H, d, J=4.5Hz), 1.27, 1.29 (6H, t, J=7Hz), 1.3-2.5 (10H, m), 3.0-4.0 (8H, m), 4.20 (4H, q, J=7Hz) |
| 59 | 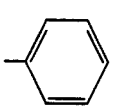 (maleate) | $[\alpha]_D^{21}$ = −28.2° (c=0.7, ethanol) | 1.1-1.6 (9H, m), 1.8-2.5 (4H, m), 2.8-3.2 (2H, m), 3.4-3.7 (2H, m), 4.18 (4H, q, J=7Hz), 6.26 (2H, s), 7.2-7.6 (5H, m) |

EXAMPLE 60

Preparation of
N-[(R)-1-ethoxycarbonyl-2-[(R,S)-1-carboxyhexylthio]ethyl]-(R,S)-alanyl-(S)-proline and di-L-arginine salt thereof The same reaction and treatment as in Reference Example 22 were repeated using 500 mg of the t-butyl ester of N-[(R)-1-ethoxycarbonyl-2-[(R,S)-1-t-butoxycarbonylhexylthio]ethyl]-(R,S)-alanyl-(S)-proline obtained in Example 54 and the resulting residue was purified by silica gel column chromatography (using a 10:1 mixture of chloroform and methanol as an eluent), giving the title compound as a colorless oil. Yield 187 mg.

$^1$H-NMR (CD$_3$OD): δ: 0.88 (3H, t, J=5 Hz), 1.28 (3H, t, J=7 Hz), 1.3–2.4 (15H, m), 2.8–3.8 (8H, m), 3.48 (1H, s), 4.21 (2H, q, J=7 Hz).

The general procedure of Example 55 was following using 72 mg of the compound obtained by the foregoing reaction and 56 mg (2 equivalents) of L-arginine, thereby giving the di-L-arginine salt of the title compound as colorless powder. Yield 110 mg. Colorless crystal, M.p. 92°–97° C.

$[α]_D^{20} = -16.5°$ (c=0.6, ethanol).

EXAMPLE 61

Preparation of
N-[(R)-1-carboxy-2-[(R,S)-1-carboxyhexylthio]ethyl]-(R,S)-alanyl-(S)-proline A 3.3 ml quantity of 1N aqueous solution of sodium hydroxide was added to a solution of 472 mg of the N-[(R)-1-ethoxycarbonyl-2-[(R,S)-1-ethoxycarbonylhexylthio]ethyl]-(R,S)-alanyl-(S)-proline obtained in Example 55 in 3 ml of ethanol. The mixture was stirred at room temperature for 2.5 hours. A small amount of water was added to the reaction mixture. The resulting mixture was applied to a column (Dowex 50W-X8(H+)). The reaction mixture was sufficiently washed with water and eluted with a 4% aqueous solution of pyridine. The fractions of the reaction product were lyophilized. The powder thus obtained was collected, washed with ether and dried under reduced pressure, giving the title compound as colorless crystals. Yield 106 mg. Colorless crystal, M.p. 98°–104° C.

$[α]_D^{20} = -66.8°$ (c=0.48, ethanol)

$^1$H-NMR (CD$_3$OD): δ: 0.9 (3H, t, J=5 Hz), 1.1–2.5 (15H, m), 2.9–3.9 (5H, m), 4.1–4.6 (3H, m).

REFERENCE EXAMPLE 30

Preparation of
N-[(R)-1-ethoxycarbonyl-2-[(R,S)-1-ethoxycarbonylheptylthio]ethyl]-(R,S)-alanine The same reaction and treatment as in Reference 24 were repeated using 11.3 g of ethyl ester of S-[(R,S)-1-ethoxycarbonylheptyl]-L-cysteine, 15.6 g of pyruvic acid, a 4N aqueous solution of sodium hydroxide and 4.5 g of sodium cyanoborohydride, thereby producing the title compound as colorless crystals.
Yield 6.8 g.

$[α]_D^{20} = -3.1°$ (c=1.2, ethanol).

$^1$H-NMR (CDCl$_3$): δ: 0.88 (3H, t, J=5 Hz), 1.2–1.5 (9H, m), 1.3–2.1 (10H, m), 2.7–3.8 (5H, m), 4.20 (4H, q, J=7 Hz).

EXAMPLE 62

Preparation of t-butyl ester of
N-[(R)-1-ethoxycarbonyl-2-[(R,S)-1-ethoxycarbonylheptylthio]ethyl]-(R,S)-alanyl-(S)-proline The general procedure of Example 45 was followed using 900 mg of the N-[(R)-1-ethoxycarbonyl-2-[(R,S)-1-ethoxycarbonylheptylthio]ethyl]-(R,S)-alanine obtained in Reference Example 30, thereby producing the title compound as a colorless oil. Yield 1.1 g.

$[α]_D^{25} = -28.6°$ (c=0.7, ethanol).

$^1$H-NMR (CDCl$_3$): δ: 0.88 (3H, t, J=5 Hz), 1.2–1.4 (9H, m), 1.44, 1.47 (total 9H, each s), 1.5–2.3 (14H, m) 2.7–3.0 (2H, m), 3.1–3.8 (5H, m), 4.19 (4H, q, J=7 Hz), 4.0–4.3 (1H, m).

EXAMPLE 63

Preparation of
N-[(R)-1-ethoxycarbonyl-2-[(R,S)-1-ethoxycarbonylheptylthio]ethyl]-(R,S)-alanyl-(S)-proline and maleate thereof The general procedure of Reference Example 22 was followed using 900 mg of the t-butyl ester of N-[(R)-1-ethoxycarbonyl-2-[(R,S)-1-ethoxycarbonylheptylthio]ethyl]-(R,S)-alanyl-(S)-proline obtained in Example 62, thereby producing the title compound as colorless amorphous substance. Yield 650 mg.

The maleate of the title compound was prepared from 230 mg of the compound resulting from the foregoing reaction by following the general procedure of Example 47. Yield 250 mg.

$[α]_D^{25} = -25.1°$ (c=0.6, ethanol).

$^1$H-NMR (CD$_3$OD): δ: 0.9 (3H, t, J=5 Hz), 1.1–1.6 (9H, m), 1.6–2.4 (14H, m), 3.1–3.9 (7H, m), 4.21 (4H, q, J=7 Hz), 4.2–4.5 (1H, m), 6.28 (2H, s).

REFERENCE EXAMPLE 31

Preparation of t-butyl ester of
N-[(R)-1-ethoxycarbonyl-2-(1-ethoxycarbonylhexylthio)ethyl]-alanine (A- and B-isomers)

In 20 ml of HMPA were dissolved 6.1 g of ethyl ester of S-[(R,S)-1-ethoxycarbonylhexyl]-L-cysteine and 4.2 g of t-butyl 2-bromopropionate. To the solution was added 2.0 g of triethylamine. The mixture was stirred at room temperature for 72 hours. Ice water was added to the reaction mixture which was then extracted with ethyl acetate. The extract was washed sequentially with water and with a saturated aqueous solution of sodium chloride and dried over anhydrous sodium sulfate. The extract was distilled under reduced pressure and the residue was separated and purified by silica gel column chromatography (using a 1:3 mixture of ether and n-hexane as an eluent), giving the A-isomer of the title compound as a colorless oil from the first eluate. Yield 2.2 g.

$[α]_D^{18} = +13.0°$ (c=1.0, ethanol).

$^1$H-NMR (CDCl$_3$): δ: 0.88 (3H, t, J=7 Hz), 1.27 (3H, d, J=7 Hz), 1.28 (6H, t, J=7 Hz), 1.45 (9H, s), 1.3–1.9(8H, m), 2.23 (1H, s), 2.7–3.0 (2H, m), 3.2–3.6 (3H, m), 4.20 (4H, q, J=7 Hz).

The B-isomer of the title compound was produced as a colorless oil from the second eluate.
Yield 1.7 g.

$[α]_D^{18} = -30.8°$ (c=1.2, ethanol).

$^1$H-NMR (CDCl$_3$): δ: 0.88 (3H, t, J=7 Hz), 1.28 (3H, d, J=7 Hz), 1.28 (6H, t, J=7 Hz), 1.3–1.9 (8H, m), 2.04

(1H, s), 2.6–3.0 (2H, m), 3.1–3.6 (3H, m), 4.20 (4H, q, J=7 Hz).

REFERENCE EXAMPLE 32

Preparation of
N-[(R)-1-ethoxycarbonyl-2-(1-ethoxycarbonylhexylthio)ethyl]-alanine (A-isomer)

A 5 ml quantity of TFA was added to 1.71 g of the t-butyl ester of N-[(R)-1-ethoxycarbonyl-2-(1-ethoxycarbonylhexylthio)ethyl]-alanine (A-isomer) obtained in Reference Example 31. The mixture was stirred at room temperature for 2 hours. The TFA was distilled off under reduced pressure. To the residue was added a saturated aqueous solution of sodium hydrogencarbonate to adjust its pH to 8. The mixture was washed with ether, adjusted to a pH of 4 by adding a 10% aqueous solution of hydrochloric acid to the aqueous layer and extracted with methylene chloride. The extract was dried over anhydrous sodium sulfate and the solvent was evaporated off under reduced pressure, giving the A isomer of the title compound. Yield 1.37 g.

$[\alpha]_D^{20} = +6.9°$ (c=0.7, ethanol).
$^1$H-NMR (CDCl$_3$): δ: 0.88 (3H, t, J=7 Hz), 1.2–1.5 (9H, m), 1.3–2.0 (8H, m), 2.9–3.9 (5H, m), 4.21 (2H, q, J=7 Hz), 4.23 (2H, q, J=7 Hz), 6.8 (1H, br s).

REFERENCE EXAMPLE 33

Preparation of
N-[(R)-1-ethoxycarbonyl-2-(1-ethoxycarbonylhexylthio)ethyl]-alanine (B-isomer)

A 5 ml quantity of TFA was added to 1.40 g of the t-butyl ester of N-[(R)-1-ethoxycarbonyl-2-(1-ethoxycarbonylhexylthio)ethyl]-alanine (B-isomer) obtained in Reference Example 31. Subsequently the same reaction and treatment as in Reference Example 32 were repeated, thereby producing the B-isomer of the title compound. Yield 1.25 g.

$[\alpha]_D^{20} = -16.2°$ (c=0.9, ethanol).
$^1$H-NMR (CDCl$_3$): δ: 0.88 (3H, t, J=7 Hz), 1.2–1.5 (9H, m), 1.3–2.0 (8H, m), 2.6–3.8 (5H, m), 4.20 (2H, q, J=7 Hz), 4.24 (2H, q, J=7 Hz), 5.8 (1H, br s).

EXAMPLE 64

Preparation of t-butyl ester of
N-[(R)-1-ethoxycarbonyl-2-(1-ethoxycarbonylhexylthio)ethyl]-alanyl-S-proline (A-isomer)

A solution of 371 mg of triethylamine in 5 ml of DMF was gradually added dropwise with ice cooling and stirring to a solution of 1.26 g of the N-[(R)-1-ethoxycarbonyl-2-(1-ethoxycarbonylhexylthio)ethyl]-alanine (A-isomer) obtained in Reference Example 32, 629 mg of t-butyl ester of (S)-proline and 666 mg of DEPC in 5 ml of DMF. The mixture was stirred for 12 hours while being allowed to slowly come to room temperature. Ice water was added to the reaction mixture and the mixture was rendered weakly alkaline with a saturated aqueous solution of sodium hydrogencarbonate and was extracted with ethyl acetate. The extract was washed sequentially with water and with a saturated aqueous solution of sodium chloride and dried over anhydrous sodium sulfate. The extract was distilled under reduced pressure and the residue was purified by silica gel column chromatography (using a 20:1 mixture of chloroform and methanol as an eluent), giving the A-isomer of the title compound as a colorless oil. Yield 1.60 g.

$[\alpha]_D^{20} = -23.1°$ (c=1.2, ethanol).
$^1$H-NMR (CDCl$_3$): δ: 0.88 (3H, t, J=7 Hz), 1.29 (3H, d, J=7 Hz), 1.29 (6H, t, J=7 Hz), 1.44, 1.47 (total 9H, each s), 1.3–2.7 (12H, m), 2.27 (1H, br s), 2.8–3.0 (2H, m), 3.1–3.8 (5H, m), 4.20 (4H, q, J=7 Hz), 4.4–4.7 (1H, m).

EXAMPLE 65

Preparation of t-butyl ester of
N-[(R)-1-ethoxycarbonyl-2-(1-ethoxycarbonylhexylthio)ethyl]-alanyl-(S)-proline (B-isomer)

The general procedure of Example 64 was followed using 1.08 g of the N-[(R)-1-ethoxycarbonyl-2-(1-ethoxycarbonylhexylthio)ethyl]-alanine (B-isomer) obtained in Reference Example 33, thereby producing the B-isomer of the title compound as a colorless oil.
Yield 1.56 g.

$[\alpha]_D^{20} = -63.7°$ (c=1.0, ethanol).
$^1$H-NMR (CDCl$_3$): δ: 0.88 (3H, t, J=7 Hz), 1.1–1.5 (9H, m), 1.44, 1.46 (total 9H, each s), 1.3–2.5 (12H, m), 2.26 (1H, br s), 2.6–3.0 (2H, m), 3.1–3.8 (5H, m), 4.20 (4H, q, J=7 Hz), 4.3–4.5 (1H, m).

EXAMPLE 66

Preparation of
N-[(R)-1-ethoxycarbonyl-2-(1-ethoxycarbonylhexylthio)ethyl]-alanyl-(S)-proline (A-isomer) and L-arginine salt thereof A 3 ml quantity of 25% HBr-acetic acid was added to 530 mg of the t-butyl ester of N-[(R)-1-ethoxycarbonyl-2-(1-ethoxycarbonylhexylthio)ethyl]-alanyl-(S)-proline (A-isomer) obtained in Example 64. The mixture was stirred at room temperature for 40 minutes. The solvent was distilled off under reduced pressure. The residue was adjusted to a pH of 8 with a saturated aqueous solution of sodium hydrogencarbonate. The resulting mixture was washed with ether. A 10% solution of hydrochloric acid was added to the aqueous layer to adjust its pH to 4. The mixture was extracted with methylene chloride. The extract was dried over anhydrous sodium sulfate and the solvent was evaporated off under reduced pressure, giving the A-isomer of the title compound as a colorless oil. Yield 452 mg.

To a solution of 242 mg of the A-isomer obtained above in 4 ml of ethanol was added with stirring 1.5 ml of an aqueous solution of 89 mg of L-arginine. The water and ethanol were distilled off, and the residue was dried under reduced pressure, giving the L-arginine salt of the title compound as pale yelow powder. Yield 143 mg.

$[\alpha]_D^{25} = -12.5°$ (c=0.3, ethanol).
$^1$H-NMR (CD$_3$OD): δ: 0.90 (3H, t, J=7 Hz), 1.2–1.5 (9H, m), 1.5–2.5 (16H, m), 2.6–3.8 (10H, m), 4.19 (4H, q, J=7 Hz), 4.3–4.5 (1H, m).

EXAMPLE 67

Preparation of
N-[(R)-1-ethoxycarbonyl-2-(1-ethoxycarbonylhexylthio)ethyl]-alanyl-(S)-proline (B-isomer) and L-arginine salt and maleate thereof The B-isomer was produced as a colorless oil from 522 mg of the t-butyl ester of N-[(R)-1-ethoxycarbonyl-2-(1-ethoxycarbonylhexylthio)ethyl]-alanyl-(S)-proline (B-isomer) obtained in Example 65 by following the general procedure of Example 66. Yield 230 mg.

The L-arginine salt of the title compound was prepared as colorless powder from 230 mg of the B-isomer obtained by the foregoing reaction by carrying out the general procedure of Example 66. Yield 270 mg.

$[\alpha]_D^{25} = -27.7°$ (c=0.3, ethanol).

$^1$H-NMR (CD$_3$OD): δ: 0.90 (3H, t, J=7 Hz), 1.2–1.5 (9H, m), 1.5–2.3 (16H, m), 2.7–3.8 (10H, m), 4.19 (4H, q, J=7 Hz), 4.3–4.5 (1H, m).

The maleate of the title compound was produced from 380 mg of the B-isomer in a similar manner as described above. Yield 382 mg.

$[\alpha]_D^{25} = -38.3°$ (c=0.7, ethanol).

$^1$H-NMR (CDCl$_3$): δ: 0.88 (3H, t, =7 Hz), 1.2–15 (9H, m), 1.5–2.5 (12H, m), 3.0–3.9 (5H, m), 4.20 (4H, q, J=7 Hz), 4.3–4.5 (1H, m), 6.32 (2H, s).

REFERENCE EXAMPLE 34

Preparation of t-butyl ester of N-[(R)-1-ethoxycarbonyl-2-(1-ethoxycarbonylheptyl-thio)ethyl]-alanine (A- and B-isomers)

The general procedure of Reference Example 31 was followed using 5.5 g of t-butyl ester of S-[(R,S)-1-ethoxycarbonylheptyl]-L-cysteine, 3.6 g of t-butyl 2-bromopropionate, 2.4 ml of triethylamine and 16 ml of HMPA, thereby giving as a colorless oil the A-isomer and B-isomer of the title compound (from the first and second eluate, respectively in the silica gel column chromatography).

A-isomer: Yield 1.9 g.

$[\alpha]_D^{23} = +18.6°$ (c=0.7, ethanol).

$^1$H-NMR (CDCl$_3$): δ: 0.87 (3H, t, J=5 Hz), 1.28 (3H, d, J=7 Hz), 1.29 (6H, t, J=7 Hz), 1.44 (9H, s), 1.3–1.8 (10H, m), 2.8–3.0 (2H, m), 3.2–3.6 (3H, m), 4.20 (4H, q, J=7 Hz).

B-isomer: Yield 1.9 g.

$[\alpha]_D^{23} = -26.0°$ (c=0.7, ethanol).

$^1$H-NMR (CDCl$_3$): δ: 0.88 (3H, t, J=5 Hz), 1.28 (3H, d, J=7 Hz), 1.29 (6H, t, J=7 Hz), 1.47 (9H, s), 1.3–2.0 (10H, m), 2.6–3.2 (2H, m), 3.2–3.6 (3H, m), 4.20 (4H, q, J=7 Hz).

REFERENCE EXAMPLE 35

Preparation of N-[(R)-1-ethoxycarbonyl-2-(1-ethoxycarbonylheptyl-thio)ethyl]-alanine (A-isomer)

The same reaction and treatment as in Reference Example 32 were repeated using 1.8 g of the t-butyl ester of N-[(R)-1-ethoxycarbonyl-2-(1-ethoxycarbonylheptylthio)ethyl]-alanine (A-isomer), thereby producing the A-isomer of the title compound. Yield 1.5 g.

$[\alpha]_D^{25} = +16.5°$ (c=0.7, ethanol).

$^1$H-NMR (CDCl$_3$): δ: 0.88 (3H, t, J=7 Hz), 1.29 (6H, t, J=7 Hz), 1.40 (3H, d, J=7 Hz), 1.5–2.1 (10H, m), 2.7–3.2 (2H, m), 3.2–3.7 (3H, m), 4.20 (4H, q, J=7 Hz), 6.41 (1H, br s).

REFERENCE EXAMPLE 36

Preparation of N-[(R)-1-ethoxycarbonyl-2-(1-ethoxycarbonylheptyl-thio)ethyl]-alanine (B-isomer)

The same reaction and treatment as in Reference Example 32 were repeated using 1.8 g of the t-butyl ester of N-[(R)-1-ethoxycarbonyl-2-(1-ethoxycarbonylheptylthio)ethyl]-alanine (B-isomer), thereby producing the B-isomer of the title compound. Yield 1.3 g.

$[\alpha]_D^{25} = -12.3°$ (c=0.6, ethanol).

$^1$H-NMR (CDCl$_3$): δ: 0.88 (3H, t, J=7 Hz), 1.30 (6H, t, J=7 Hz), 1.43 (3H, d, J=7 Hz), 1.5–2.1 (10H, m), 2.5–3.1 (2H, m), 3.1–3.5 (3H, m), 4.20 (2H, q, J=7 Hz), 4.24 (2H, q, J=7 Hz), 5.59 (1H, br s).

EXAMPLE 68

Preparation of t-butyl ester of N-[(R)-1-ethoxycarbonyl-2-(1-ethoxycarbonylheptyl-thio)ethyl]-alanyl-(S)-proline (A-isomer)

The same reaction and treatment as in Example 64 were repeated using 1.2 g of the N-[(R)-1-ethoxycarbonyl-2-(1-ethoxycarbonylheptylthio)ethyl]-alanine (A-isomer) obtained in Reference Example 35, 530 mg of t-butyl ester of (S)-proline, 550 mg of DEPC and 0.43 ml of triethylamine, thereby producing the A-isomer of the title compound as a colorless oil. Yield 1.36 g.

$[\alpha]_D^{25} = -12.4°$ (c=0.6, ethanol).

$^1$H-NMR (CDCl$_3$): δ: 0.87 (3H, t, J=7 Hz), 1.29 (6H, t, J=7 Hz), 1.31 (3H, d, J=7 Hz), 1.44, 1.47 (total 9H, each s), 1.5–2.2 (14H, m), 2.7–3.0 (2H, m), 3.1–3.9 (5H, m), 4.20 (4H, q, J=7 Hz), 4.0–4.5 (1H, m).

EXAMPLE 69

Preparation of t-butyl ester of N-[(R)-1-ethoxycarbonyl-2-(1-ethoxycarbonylheptyl-thio)ethyl]-alanyl-(S)-proline (B-isomer)

The B-isomer of the title compound was produced as a colorless oil from 1.05 g of the N-[(R)-1-ethoxycarbonyl-2-(1-ethoxycarbonylheptylthio)ethyl]-alanine (B-isomer) obtained in Reference Example 36 by following the general procedure of Example 64. Yield 1.3 g.

$[\alpha]_D^{25} = -67.5°$ (c=1.0, ethanol).

$^1$H-NMR (CDCl$_3$): δ: 0.88 (3H, t, J=7 Hz), 1.2–1.5 (9H, m), 1.44, 1.46 (total 9H, each s), 1.6–2.5 (14H, m), 2.6–3.8 (7H, m), 4.19 (4H, q, J=7 Hz), 4.2–4.5 (1H, m).

EXAMPLE 70

Preparation of N-[(R)-1-ethoxycarbonyl-2-(1-ethoxycarbonylheptyl-thio)ethyl]-alanyl-(S)-proline (A-isomer) and maleate thereof The same reaction and treatment as in Reference Example 22 were performed using 398 mg of the t-butyl ester of N-[(R)-1-ethoxycarbonyl-2-(1-ethoxycarbonyl-heptylthio)ethyl]-alanyl-(S)-proline (A-isomer) obtained in Example 68, thereby producing the A-isomer of the title compound as a colorless oil. Yield 270 mg.

The maleate of the title compound was produced from 270 mg of the compound resulting from the foregoing reaction by carrying out the general procedure of Example 47. Yield 310 mg.

$[\alpha]_D^{25} = -28.3°$ (c=0.6, ethanol).

$^1$H-NMR (CD$_3$OD): δ: 0.90 (3H, t, J=7 Hz), 1.1–1.6 (9H, m), 1.5–2.4 (14H, m), 3.0–3.9 (7H, m), 4.21 (4H, q, J=7 Hz), 6.28 (2H, s).

EXAMPLE 71

Preparation of N-[(R)-1-ethoxycarbonyl-2-(1ethoxycarbonylheptylthi-o)ethyl]-alanine-(S)-proline (B-isomer) and L-arginate and maleate thereof The general procedure of Example 66 was followed using 450 mg of the t-butyl ester of N-[(R)-1-ethoxycarbonyl-2-(1-ethoxycarbonylheptylthio)ethyl]-alanyl-(S)-proline (B-isomer) obtained in Example 69, thereby producing as colorless (amorphous) powder the L-arginine salt of the title compound. Yield 516 mg.

$[\alpha]_D^{25} = -36.9°$ (c=0.5, ethanol).

$^1$H-NMR (CDCl$_3$): δ: 0.87 (3H, t, J=7 Hz), 1.2–1.5 (9H, m), 1.5–2.5 (18H, m), 2.7–3.8 (10H, m), 4.20 (4H, q, J=7 Hz), 4.5–4.6 (1H, m).

The general procedure of Example 47 was followed using 430 mg of the t-butyl ester of N-[(R)-1-ethoxycarbonyl-2-(1-ethoxycarbonylheptylthio)ethyl]-alanyl-(S)-proline (B-isomer), thereby producing the maleate of the title compound. Yield 457 mg.

$[\alpha]_D^{25} = -38.3°$ (c=0.8, ethanol).

$^1$H-NMR (CD$_3$OD): δ: 0.90 (3H, t, J=7 Hz), 1.2–1.5 (9H, m), 1.6–2.5 (14H, m), 2.8–3.8 (7H, m), 4.22 (4H, q, J=7 Hz), 4.5–4.6 (1H, m), 6.28 (2H, s).

REFERENCE EXAMPLE 37

Preparation of t-butyl ester of N-[(R)-1-ethoxycarbonyl-2-(1-ethoxycarbonyloctylthio)ethyl]-alanine (A- and B-isomers)

In 16 ml of HMPA were dissolved 10 g of ethyl ester of S-[(RS)-1-ethoxycarbonyloctyl]-L-cysteine and 6.9 g of t-butyl 2-bromopropionate. To the solution was added 4.6 ml of triethylamine. The mixture was stirred at room temperature for 48 hours. Ice water was added to the reaction mixture. The resulting mixture was extracted with ethyl acetate. The extract was washed sequentially with water and with a saturated aqueous solution of sodium chloride and dried over anhydrous sodium sulfate. The extract was distilled under reduced pressure. The residue was separated and purified by silica gel column chromatography (using a 1:3 mixture of ether and n-hexane as an eluent), producing the A-isomer of the title compound as a colorless oil from the first eluate. Yield 2.7 g.

$[\alpha]_D^{22} = +13.2°$ (c=1.2, ethanol).

$^1$H-NMR (CDCl$_3$): δ: 0.88 (3H, t, J=7 Hz), 1.2–1.4 (9H, m), 1.45 (9H, s), 1.2–2.1 (12H, m), 2.24 (1H, br s), 2.8–3.1 (2H, m), 3.1–3.6 (3H, m), 4.20 (4H, q, J=7 Hz).

The B-isomer of the title compound was produced as a colorless oil from the second eluate. Yield 2.2 g.

$[\alpha]_D^{22} = -25.9°$ (c=0.9, ethanol).

$^1$H-NMR (CDCl$_3$): δ: 0.88 (3H, t, J=7 Hz), 1.2–1.4 (9H, m), 1.47 (9H, s), 1.2–2.2 (13H, m), 2.76 (1H, d-d, J=13 Hz, 8 Hz), 3.03 (1H, d-d, J=13 Hz, 5 Hz), 3.1–3.6 (3H, m), 4.20 (4H, q, J=7 Hz).

REFERENCE EXAMPLES 38 AND 39

The compounds as shown below in Table 15 were produced by following the general procedure of Reference Example 37

TABLE 15

$$\begin{array}{c} R_5 \quad\quad\quad\quad\quad CH_3 \\ | \quad\quad (R) \quad | \\ CH-SCH_2-CH-N-CH-CO_2-C(CH_3)_3 \\ | \quad\quad\quad | \quad H \\ CO_2C_2H_5 \quad CO_2C_2H_5 \end{array}$$

| Ref. Ex. No. | R$_5$ | Isomer | Optical Rotation (Solvent: ethanol) | $^1$H—NMR (CDCl$_3$):δ |
|---|---|---|---|---|
| 38 | CH$_3$(CH$_2$)$_8$— | A | $[\alpha]_D^{23} =$ +16.9° (c=1.0) | 0.89 (3H, t, J=7Hz), 1.2–1.4 (9H, m), 1.45 (9H, s), 1.2–1.9 (16H, m), 2.26 (1H, br s), 2.8–3.0 (2H, m), 3.2–3.6 (3H, m), 4.20 (4H, q, J=7Hz) |
| | | B | $[\alpha]_D^{23} =$ −22.8° (c=0.7) | 0.88 (3H, t, J=7Hz), 1.2–1.4 (9H, m), 1.47 (9H, s), 1.2–2.0 (16H, m), 2.6–3.1 (2H, m), 3.1–3.6 (3H, m), 4.20 (4H, q, J=7Hz) |
| 39 | CH$_3$(CH$_2$)$_{10}$— | A | $[\alpha]_D^{21} =$ +8.9° (c=1.4) | 0.88 (3H, t, J=7Hz), 1.25 (6H, t, J=7Hz), 1.33 (3H, d, J=7Hz), 1.45 (9H, s), 1.2–2.1 (20H, m), 2.06 (1H, br s), 2.7–3.0 (2H, m), 3.1–3.6 (3H, m), 4.20 (4H, q, J=7Hz) |
| | | B | $[\alpha]_D^{21} =$ −23.0° (c=1.0) | 0.88 (3H, t, J=7Hz), 1.25 (6H, t, J=7Hz), 1.33 (3H, d, J=7Hz), 1.46 (9H, s), 1.2–2.2 (20H, m), 1.88 (1H, br s), 2.7–3.6 (5H, m), 4.20 (4H, q, J=7Hz) |

REFERENCE EXAMPLE 40

Preparation of N-[(R)-1-ethoxycarbonyl-2-(1-ethoxycarbonyloctylthio)ethyl]-alanine (B-isomer)

In 6 ml of 25% HBr-acetic acid was dissolved 2.2 g of B-isomer of the t-butyl ester of N-[(R)-1-ethoxycarbonyl-2-(1-ethoxycarbonyloctylthio)ethyl]-alanine (B-isomer) obtained in Reference Example 37. The mixture was stirred at room temperature for 40 minutes. The HBr-acetic acid was distilled off under reduced pressure. The residue was adjusted to a pH of 8 with a saturated aqueous solution of sodium hydrogencarbonate and the mixture was washed with ether. Citric acid was added to the aqueous layer to adjust its pH to 4, and the mixture was extracted with methylene chloride. The extract was dried over anhydrous sodium sulfate and the solvent was evaporated off under reduced pressure, giving the title compound. Yield 1.8 g.

$[\alpha]_D^{22} = -15.7°$ (c=0.8, ethanol).

$^1$H-NMR (CDCl$_3$): δ: 0.88 (3H, t, J=7 Hz), 1.30 (6H, t, J=7 Hz), 1.43 (3H, d, J=7 Hz), 1.2–2.1 (13H, m), 2.3–3.5 (5H, m), 4.20 (2H, q, J=7 Hz), 4.23 (2H, q, J=7 Hz), 5.25 (1H, br s).

REFERENCE EXAMPLES 41 AND 42

The compounds as shown below in Table 16 were produced by following the general procedure of Reference Example 40.

TABLE 16

$$\begin{array}{c} R_5 \quad\quad\quad\quad\quad CH_3 \\ | \quad\quad (R) \quad\quad | \\ CH-SCH_2-CH-N-CH-CO_2H \\ | \quad\quad\quad\quad | \quad H \\ CO_2C_2H_5 \quad CO_2C_2H_5 \end{array}$$

| Ref. Ex. No. | $R_5$ | Isomer | Optical Rotation (Solvent: ethanol) | $^1$H—NMR (CDCl$_3$): δ |
|---|---|---|---|---|
| 41 | $CH_3(CH_2)_8$ | B | $[\alpha]_D^{23} = -12.4°$ (c = 0.7) | 0.88(3H, t, J=7Hz), 1.2–1.5(9H, m), 1.2–2.1(17H, m), 2.5–3.1(2H, m), 3.1–3.5(3H, m), 4.23(2H, q, J=7Hz), 4.28(2H, q, J=7Hz), 5.10(1H, brs) |
| 42 | $CH_3(CH_2)_{10}$ | B | $[\alpha]_D^{20} = -13.4°$ (c = 1.0) | 0.88(3H, t, J=7Hz), 1.2–1.4(9H, m), 1.2–2.2(21H, m), 2.5–3.6(5H, m), 4.20(2H, q, J=7 Hz), 4.23(2H, q, J=7 Hz), 5.50(1H brs) |

EXAMPLE 72

Preparation of t-butyl ester of N-[(R)-1-ethoxycarbonyl-2-(1-ethoxycarbonyloctylthio)ethyl]-alanyl-(S)-proline (B-isomer)

A solution of 417 mg of triethylamine in 5 ml of DMF was gradually added dropwise with ice cooling and stirring to a solution of 1.52 g of the N-[(R)-1-ethoxycarbonyl-2-(1-ethoxycarbonyloctylthio)ethyl]-alanine (B-isomer) obtained in Reference Example 40, 705 mg of t-butyl ester of (S)-proline and 747 mg of DEPC (90% content) in 30 ml of DMF. The mixture was further stirred for 12 hours while being allowed to slowly come to room temperature. The reaction mixture was poured into ice water and extracted with ethyl acetate. The extract was washed with water and dried over anhydrous sodium sulfate. The extract was distilled under reduced pressure and the residue was purified by silica gel column chromatography (using a 35:1 mixture of chloroform and methanol as an eluent), giving the title compound as a colorless oil. Yield 2.08 g.

$[\alpha]_D^{20} = -60.6°$ (c=1.5, ethanol).

$^1$H-NMR (CDCl$_3$): δ: 0.88 (3H, t, J=7 Hz), 1.28 (6H, t, J=7 Hz), 1.30 (3H, d, J=7 Hz), 1.44, 1.46 (total 9H, each s), 1.2–2.5 (17H, m), 2.6–3.7 (7H, m), 4.19 (4H, q, J=7 Hz), 4.4–4.5 (1H, m).

EXAMPLES 73 AND 74

The compounds as shown below in Table 17 were produced by following the general procedure of Example 72.

TABLE 17

$$\begin{array}{c} R_5 \quad\quad\quad\quad\quad CH_3 \\ | \quad\quad (R) \quad\quad | \\ CH-SCH_2-CH-N-CH-CO-N \\ | \quad\quad\quad\quad | \quad H \\ CO_2C_2H_5 \quad CO_2C_2H_5 \quad\quad (S) \\ \quad\quad\quad\quad\quad\quad\quad\quad CO_2-C(CH_3)_3 \end{array}$$

| Example No. | $R_5$ | Isomer | Optical Rotation (Solvent: ethanol) | $^1$H—NMR (CDCl$_3$): δ |
|---|---|---|---|---|
| 73 | $CH_3(CH_2)_8$ | B | $[\alpha]_D^{23} = -58.6°$ (c = 0.7) | 0.88(3H, t, J=7Hz), 1.2–1.4(9H, m), 1.2–2.4(21H, m), 1.44, 1.46(total 9H, each s), 2.6–3.8(7H, m), 4.19(4H, q, J=7Hz), 4.3–4.5(1H, m) |
| 74 | $CH_3(CH_2)_{10}$ | B | $[\alpha]_D^{19} = -60.0°$ (c = 0.9) | 0.88(3H, t, J=7Hz), 1.2–1.4(9H, m), 1.44, 1.49(total 9H, each s), 1.2–2.3(25H, m), 2.25(1H, br.s), 2.6–3.7(7H, m), 4.19(4H, q, J=7Hz), 4.4–4.5(1H, m) |

EXAMPLE 75

Preparation of N-[(R)-1-ethoxycarbonyl-2-(1-ethoxycarbonyloctylthio)ethyl]-alanyl-(S)-proline (B-isomer) and L-arginine salt thereof The general procedure of Reference Example 40 was followed using 2.1 g of the t-butyl ester of N-[(R)-1-ethoxycarbonyl-2-(1-ethoxycarbonyloctylthio)ethyl]-alanyl-(S)-proline (B-isomer) obtained in Example 72, thereby producing the title compound as a colorless oil. Yield 1.0 g.

A solution of 650 mg of L-arginine in 10 ml of water was added to a solution of 1.0 g of the compound resulting from the above reaction in 20 ml of ethanol. The mixture was distilled under reduced pressure. Ethanol was added to the residue and distilled off under reduced pressure. This procedure was repeated several times. The residue was recrystallized from a mixture of ethyl acetate and n-hexane, giving the L-arginine salt of the title compound. Yield 400 mg.

$[\alpha]_D^{22} = -42.0°$ (c=0.6, ethanol).

$^1$H-NMR (CD$_3$OD): δ: 0.89 (3H, t, J=7 Hz), 1.2–1.4 (9H, m), 1.2–2.2 (20H, m), 2.5–3.7 (10H, m), 4.18 (4H, q, J=7 Hz), 4.3–4.5 (1H, m).

EXAMPLES 76 AND 77

The compounds as shown below in Table 18 were prepared by following the general procedure of Example 75.

TABLE 18

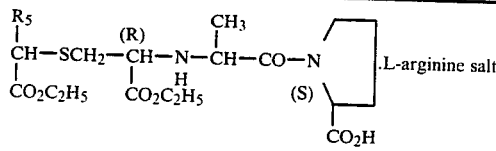.L-arginine salt

| Example No. | R$_5$ | Isomer | Optical Rotation (Solvent: ethanol) | $^1$H—NMR (CDCl$_3$): δ |
|---|---|---|---|---|
| 76 | CH$_3$(CH$_2$)$_8$ | B | $[\alpha]_D^{23} = -38.1°$ (c = 0.7) | 0.90(3H, t, J=7Hz), 1.2–1.4(9H, m), 1.2–2.2(24H, m), 2.8–3.8(10H, m), 4.19(4H, q, J=7Hz), 4.2–4.5(1H, m) |
| 77 | CH$_3$(CH$_2$)$_{10}$ | B | $[\alpha]_D^{19} = -36.2°$ (c = 0.9) | 0.90(3H, t, J=7Hz), 1.2–1.4(9H, m), 1.2–2.2(28H, m), 2.6–3.7(10H, m), 4.19(4H, q, J=7Hz), 4.3–4.5(1H, m) |

EXAMPLES 78 AND 79

The compounds as shown below in Table 19 were produced by following the general procedure of Example 65.

TABLE 19

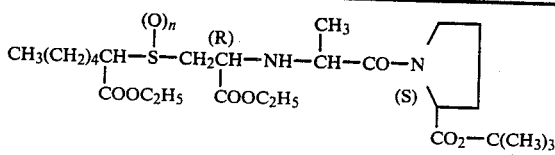

| Example No. | n | Isomer | Optical Rotation (Solvent: ethanol) | $^1$H—NMR (CDCl$_3$): δ |
|---|---|---|---|---|
| 78 | 1 | B | $[\alpha]_D^{20} = -87.2°$ (c = 1.8) | 0.89(3H, t, J=7Hz), 1.1–1.5(9H, m), 1.39, 1.44(total 9H, each s), 1.3–2.5(13H, m), 3.12(2H, d, J=7Hz), 3.4–3.9(5H, m), 4.19(4H, q, J=7Hz), 4.2–4.5(1H, m) |
| 79 | 2 | B | $[\alpha]_D^{20} = -58.6°$ (c = 1.7) | 0.89(3H, t, J=7Hz), 1.2–1.5(9H, m), 1.37, 1.49(total 9H, each s), 1.4–2.4(13H, m), 3.4–4.0(6H, m), 4.20, (4H, q, J=7Hz), 4.1–4.5(2H, m) |

EXAMPLE 80

Preparation of t-butyl ester of N-[(R)-1-ethoxycarbonyl-2-octylthio-ethyl]-alanyl-(S)-proline (β-isomer)

The title compound was prepared from suitable starting materials by following the general procedure of Example 13.

$[\alpha]_D^{25} = -85.7°$ (c=0.7, ethanol).

$^1$H-NMR (CDCl$_3$): δ: 0.88 (3H, t, J=5 Hz), 1.28 (3H, t, J=7 Hz), 1.29 (3H, d, J=6 Hz), 1.2–1.8 (12H, m), 1.44, 1.46 (total 9H, each s), 1.8–2.3 (4H, m), 2.52 (2H, t, J=7 Hz), 2.70 (1H, d-d, J=13 Hz, 7.5 Hz), 2.89 (1H, d-d, J=13 Hz, 6 Hz), 3.2–3.7 (4H, m), 4.2 (2H, q, J=7 Hz), 4.3–4.5 (1H, m).

EXAMPLE 81

Preparation of N-[(R)-1-ethoxycarbonyl-2-octylthio-ethyl]-alanyl-(S)-proline (β-isomer).L-arginine salt The title compound was prepared from suitable materials by following the general procedure of Example 17.

$[\alpha]_D^{25} = -56.5°$ (c=0.5, ethanol).
M.p. 70°–81° C.

REFERENCE EXAMPLES 43 AND 44

The compounds as shown below in Table 20 were prepared by following the general procedure of Reference Example 8.

REFERENCE EXAMPLES 45 AND 46

The compounds as shown below in Table 21 were prepared by following the general procedure of Reference Example 13.

TABLE 21

$$CH_3(CH_2)_6SCH_2\overset{(R)}{\underset{COOR_2}{C}}HNH\overset{CH_3}{\underset{*}{C}}HCOY$$

| Ref. Ex. No. | $R_2$ | Y | Isomer (*) | Optical Rotation (Solvent: ethanol) | Melting point (°C.) |
|---|---|---|---|---|---|
| 45 | —CH(CH$_3$)$_2$ | —OH | β | $[\alpha]_D^{25} = -20.0°$ (c = 0.7) | 115–120 |
| 46 | —CH$_2$CH(CH$_3$)$_2$ | —OH | β | $[\alpha]_D^{25} = -21.2°$ (c = 0.7) | 114–117 |

TABLE 20

$$CH_3(CH_2)_6SCH_2\overset{(R)}{\underset{COOR_2}{C}}H-NH\overset{CH_3}{\underset{*}{C}}HCOY$$

| Ref. Ex. No. | $R_2$ | Y | Isomer (*) | Optical Rotation (Solvent: ethanol) | $^1$H—NMR (CDCl$_3$): δ |
|---|---|---|---|---|---|
| 43 | —CH(CH$_3$)$_2$ | —OC(CH$_3$)$_3$ | β | $[\alpha]_D^{25} = -29.6°$ (c = 0.9) | 0.88(3H, t, J=5.5Hz), 1.27(6H, d, J=5.9Hz), 1.29(3H, d, J=7.0Hz), 1.47(9H, s), 1.10–1.80(10H, m), 2.54(2H, t, J=6.5Hz), 2.68(1H, d—d, J=13.0Hz, 7.5Hz), 2.92(1H, d—d, J=13.0Hz, 5.5Hz), 3.28(1H, q, J=7.0Hz), 3.42(1H, d—d, J=7.5Hz, 5.5Hz), 5.08(1H, sept, J=5.9Hz) |
| 44 | —CH$_2$CH(CH$_3$)$_2$ | —OC(CH$_3$)$_3$ | β | $[\alpha]_D^{25} = -28.3°$ (c = 1.0) | 0.88(3H, t, J=5.5Hz), 0.95(6H, d, J=6.6Hz), 1.29(3H, d, J=6.8Hz), 1.46(9H, s), 1.10–1.80(10H, m), 1.75–2.24(1H, m), 2.54(2H, t, J=6.8Hz), 2.68(1H, d—d, J=13.0Hz, 7.5Hz), 2.93(1H, d—d, J=13.0Hz, 5.5Hz), 3.30(1H, q, J=7.0Hz), 3.47(1H, d—d, J=7.5Hz, 5.5Hz), 3.93(2H, d, J=6.6Hz) |

EXAMPLES 82 AND 83

The compounds as shown below in Table 22 were prepared by following the general procedure of Example 13.

TABLE 22

$$CH_3(CH_2)_6SCH_2\overset{(R)}{\underset{COOR_2}{C}}HNH\overset{CH_3}{\underset{*}{C}}HCOY$$

| Example No. | $R_2$ | Y | Isomer (*) | Optical Rotation (Solvent: ethanol) | $^1$H—NMR(CDCl$_3$): δ |
|---|---|---|---|---|---|
| 82 | —CH(CH$_3$)$_2$ | —N(S)-prolinate-COOC(CH$_3$)$_3$ | β | $[\alpha]_D^{25} = -75.7°$ (c = 0.9) | 0.88(3H, t, J=5.5Hz), 1.26(6H, d, J=6.4Hz), 1.28(3H, d, J=6.6Hz), 1.44, 1.46(total 9H, each s), 1.05–1.76(10H, m), 1.76–2.40(4H, m), 2.52(2H, t, J=6.8Hz), 2.68(1H, d—d, J=13.0Hz, 7.5Hz), 2.92(1H, d—d, J=13.0Hz, 5.5Hz), 3.20–3.76(4H, m), 4.01–1.54(1H, m), 5.07(1H, sept, J=6.4Hz) |

TABLE 22-continued $$CH_3(CH_2)_6SCH_2\overset{(R)}{\underset{COOR_2}{C}}HNH\overset{CH_3}{\underset{*}{C}}HCOY$$

| Example No. | $R_2$ | Y | Isomer (*) | Optical Rotation (Solvent: ethanol) | $^1H$—NMR(CDCl$_3$): δ |
|---|---|---|---|---|---|
| 83 | —CH$_2$CH(CH$_3$)$_2$ | —N(S)⟩COOC(CH$_3$)$_3$ (pyrrolidine) | β | $[\alpha]_D^{25} = -86.0°$ (c = 0.8) | 0.88(3H, t, J=5.5Hz), 0.94(6H, d, J=6.8Hz), 1.30(3H, d, J=6.8Hz), 1.44, 1.46(total 9H, each s), 1.10-1.73(10H, m), 1.75-2.28(5H, m), 2.52(2H, t, J=7.0Hz), 2.69(1H, d—d, J=13.0Hz, 7.5Hz), 2.92(1H, d—d, J=13.0Hz, 5.5Hz), 3.30-3.65(4H, m), 3.92(2H, d, J=6.8Hz), 4.05-4.59(1H, m) |

EXAMPLES 84 AND 85

The compounds as shown below in Table 23 were prepared by following the general procedure of Example 18.

TABLE 23

$$CH_3(CH_2)_6SCH_2\overset{(R)}{\underset{COOR_2}{C}}HNH\overset{CH_3}{\underset{*}{C}}HCOY$$

| Example No. | $R_2$ | Y | Isomer (*) | Optical Rotation (Solvent: ethanol) | Melting point (°C.) |
|---|---|---|---|---|---|
| 84 | —CH(CH$_3$)$_2$ | —N(S)⟩COOH | β | $[\alpha]_D^{25} = -61.2°$ (c = 0.5) | 103-104 (maleate) |
| 85 | —CH$_2$CH(CH$_3$)$_2$ | —N(S)⟩COOH | β | $[\alpha]_D^{25} = -60.7°$ (c = 0.6) | 110-111 (maleate) |

REFERENCE EXAMPLES 47 AND 48

The compounds as shown below in Table 24 were prepared by following the general procedure of Reference Example 8.

TABLE 24

$$CH_3(CH_2)_7SCH_2\overset{(R)}{\underset{CO_2C_2H_5}{C}}H-NH-\overset{CH_3}{\underset{*}{C}}H-CO_2C(CH_3)_3$$

| Ref. Ex. No. | Isomer (*) | Optical Rotation (Solvent: ethanol) | $^1H$—NMR(CDCl$_3$): δ |
|---|---|---|---|
| 47 | α | $[\alpha]_D^{25} = +25.4°$ (c = 0.7) | 0.88(3H, t, J=7Hz), 1.27(3H, d, J=7Hz), 1.29(3H, t, J=7Hz), 1.2-1.8(12H, m), 1.45(9H, s), 2.55(2H, t, J=7Hz), 2.80(2H, d, J=6Hz), 3.32(1H, q, J=7Hz), 3.46(1H, t, J=7Hz), |
| 48 | β | $[\alpha]_D^{25} = -34.7°$ (c = 0.6) | 4.20(2H, q, J=7Hz) 0.88(3H, t, J=7Hz), 1.29(3H, t, J=7Hz), 1.30(3H, d, J=7Hz), 1.2-1.9(12H, m), 1.47(9H, s), 2.54(2H, t, J=7Hz), 2.68(1H, d—d, J=13Hz, 7.5Hz), 2.92(1H, d—d, J=13Hz, 5.5Hz), 3.29(1H, q, J=7=7Hz) 3.46(1H, d—d, J=7.5Hz, 5.5Hz), 4.21(2H, q, J=7Hz) |

REFERENCE EXAMPLE 49

The compound as shown below was produced by following the general procedure of Reference Example 13.

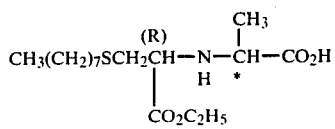

β-isomer.
$[\alpha]_D^{25} = -23.2°$ (c=0.6, DMF).
M.p. 125°–127° C.

PREPARATION EXAMPLE 1

Preparation of tablets

One thousand tablets for oral administration each containing 5 mg of the maleate of N-[(R)-1-ethoxycarbonyl-2-heptylthio)ethyl]-alanyl-(S)-proline (β-isomer) were prepared according to the following formulation.

| Component | Amount (g) |
| --- | --- |
| Maleate of N—[(R)—1-ethoxycarbonyl-2-heptylthioethyl]-alanyl-(S)—proline (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The maleate of N-[(R)-1-ethoxycarbonyl-2-heptylthioethyl]-alanyl-(S)-proline (β-isomer), lactose, corn starch and crystalline cellulose were thoroughly mixed together and granulated with a 5% aqueous solution of methyl cellulose. The granulues thus obtained were passed through a 200-mesh sieve and mixed with magnesium stearate and the mixture was pressed into tablets.

PREPARATION EXAMPLE 2

Preparation of capsules

One thousand hard gelatin capsules for oral administration each containing 10 mg of the maleate of N-[(R)-1-ethoxycarbonyl-2-heptylthioethyl]-alanyl-(S)-proline (β-isomer) were prepared according to the following formulation.

| Component | Amount (g) |
| --- | --- |
| Maleate of N—[(R)—1-ethoxycarbonyl-2-heptylthioethyl]-alanyl-(S)—proline (β-isomer) | 10 |
| Lactose (according to Japanese Pharmacopoeia) | 80 |
| Starch (according to Japanese Pharmacopoeia) | 30 |
| Talc (according to Japanese Pharmacopoeia) | 5 |
| Magnesium stearate (according to Japanese Pharmacopoeia) | 1 |

The foregoing components were finely divided and thoroughly stirred to obtain a homogeneous mixture. The mixture was enclosed in capsules for oral administration having the desired size.

PREPARATION EXAMPLE 3

Preparation of injections

A sterilized aqueous solution for parental administration was prepared according to the following formulation.

| Component | Amount (g) |
| --- | --- |
| Maleate of N—[(R)—1-ethoxycarbonyl-2-heptylthioethyl]-alanyl-(S)—proline (β-isomer) | 1 |
| Polyethylene glycol having molecular weight of 4000 (according to Japanese Pharmacopoeia) | 0.3 |
| Sodium chloride (according to Japanese Pharmacopoeia) | 0.9 |
| Polyoxyethylene sorbitan monooleate (according to Japanese Pharmacopoeia) | 0.4 |
| Sodium metabisulfite | 0.1 |
| Methylparaben (according to Japanese Pharmacopoeia) | 0.18 |
| Propylparaben (according to Japanese Pharmacopoeia) | 0.02 |
| Distilled water for injection | 100 (ml) |

The foregoing parabens, sodium metabisulfite and sodium chloride were dissolved at 80° C. in about 50 ml of distilled water for injection while being stirred. The solution was cooled to 40° C. In the solution were dissolved the maleate of N-[(R)-1-ethoxycarbonyl-2-heptylthioethyl]-alanyl-(S)-proline (β-isomer), and then the polyethylene glycol and polyoxyethylene sorbitan monooleate. Distilled water for injection (about 50 ml) was added to the solution to adjust the final regulated volume, and the mixture was sterilized by sterile filtration by using a suitable filter paper. One mililiter of the solution was introduced into separate ampoules to make injectables.

PREPARATION EXAMPLE 4

Preparation of tablets

One thousand tablets for oral administration each containing 5 mg of t-butyl ester of N-[(R)-1-ethoxycarbonyl-2-hexylthioethyl]-alanyl-(S)-proline (β-isomer) were prepared according to the following formulation.

| Component | Amount (g) |
| --- | --- |
| T-Butyl ester of N—[(R)—1-ethoxycarbonyl-2-hexylthioethyl]-alanyl-(S)—proline (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The t-butyl ester of N-[(R)-1-ethoxycarbonyl-2-hexylthioethyl]-alanyl-(S)-proline (β-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PREPARATION EXAMPLE 5

Preparation of tablets

One thousand tablets for oral administration each containing 5 mg of maleate of methyl ester of N-[(R)-1-ethoxycarbonyl-2-heptylthioethyl]-alanyl-(S)-proline (β-isomer) were prepared according to the following formulation.

| Component | Amount (g) |
|---|---|
| Maleate of methyl ester of N—[(R)—1-ethoxycarbonyl-2-heptylthioethyl]-alanyl-(S)—proline (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The maleate of methyl ester of N-[(R)-1-ethoxycarbonyl-2-heptylthioethyl]-alanyl-(S)-proline (β-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

PREPARATION EXAMPLE 6

Preparation of tablets

One thousand tablets for oral administration each containing 5 mg of L-arginine salt of N-[(R)-1-ethoxycarbonyl-2-(1-ethoxycarbonylhexylthio)ethyl]-alanyl-(S)-proline (B-isomer) were prepared according to the following formulation.

| Component | Amount (g) |
|---|---|
| L-Arginine salt of N—[(R)—1-ethoxycarbonyl-2-(1-ethoxycarbonylhexylthio)ethyl]-alanyl-(S)—proline (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The L-arginine salt of N-[(R)-1-ethoxycarbonyl-2-(1-ethoxycarbonylhexylthio)ethyl]-alanyl-(S)-proline (B-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

TEST EXAMPLE 1

Inhibitory activity against angiotensin-converting enzyme (ACE)

A 100 μl quantity of an enzyme solution prepared from rabbit lung acetone powder (product of Sigma Chemical Co., Ltd., U.S.A.) was mixed with 100 μl of a sample solution. The mixture was gently shaken at 37° C. for 10 minutes. To the reaction mixture was added 100 μl of a solution containing 6.99 mM of hippurylhistidyl-leucine (product of Peptide Institute, Inc., Japan) as a substrate. The mixture was reacted at 37° C. for 45 minutes while being shaken. The reaction was terminated by addition of 200 μl of a 1N sulfuric acid aqueous solution to the reaction mixture. Sodium chloride (saturation amount) and diethyl ether (2 ml) were added to the reaction mixture to extract the hippuric acid formed by the reaction. The resulting mixture was vigorously shaken for 15 minutes and centrifuged at 2000 rpm for 5 minutes. A 1.5 ml quantity of the ether layer was separated. After the solvent was distilled off, the residue was redissolved in 1.5 ml of distilled water and the absorbance at 228 nm was measured. A control was prepared by repeating the same procedure as above except that 100 μl of distilled water was used in place of the sample solution.

The inhibitory activity was calculated by deducting the absorbance value of the residue formed by addition of the sample solution from that of the control, and the resulting value was divided by the absorbance value of the control and multiplied by 100, thereby giving a percent inhibition. The inhibitory activity was expressed as $IC_{50}$, i.e., the concentration of the sample solution in the reaction mixture in which concentration 50% inhibition is achieved.

The test compounds used in the experiment are shown below. The test result is given below in Table 25.

| Test Compound No. | Name of Test Compounds |
|---|---|
| 1 | N—[(R)—1-carboxy-2-hexylthioethyl]-alanyl-(S)—proline (β-isomer) (compound obtained in Example 10) |
| 2 | N—[(R)—1-carboxy-2-hexylthioethyl]-(RS)—alanyl-(S)—proline (compound obtained in Example 11) |
| 3 | N—[(R)—1-carboxy-2-pentylthioethyl]-alanyl-(S)—proline (β-isomer) (compound obtained in Example 12) |
| 4 | N—[(S)—1-carboxy-3-methylthiopropyl]-(R,S)—alanyl-(S)—proline (corresponding to the compound produced in Example 17 of Japanese Unexamined Patent Publication No. 81845/1980) |
| 5 | N—[(S)—1-methoxycarbonyl-3-methylthiopropyl]-(R,S)—alanyl-(S)—proline hydrochloride (corresponding to the hydrochloride of the compound produced in Example 16 of Japanese Unexamined Patent Publication No. 81845/1980) |

TABLE 25

| Test Compound No. | ACE inhibitory activity $IC_{50}$ (mol/liter) |
|---|---|
| 1 | $5.21 \times 10^{-10}$ |
| 2 | $1.35 \times 10^{-9}$ |

TABLE 25-continued

| Test Compound No. | ACE inhibitory activity $IC_{50}$ (mol/liter) |
|---|---|
| 3 | $1.04 \times 10^{-10}$ |
| 4 | $1.27 \times 10^{-8}$ |
| 5 | $5.24 \times 10^{-6}$ |

Table 25 shows that the test compounds of the present invention exhibited the ACE inhibitory activity higher than Test Compound No. 4 having the highest inhibitory activity. More specifically, Test Compounds 1, 2 and 3 were higher in this respect by about 24 times, about 9.4 times and about 122 times respectively, than Test Compound No. 4.

TEST EXAMPLE 2

ACE Inhibitory effect in normotensive rats

Male Wistar rats weighing 200 to 400 g were anesthetized by the intraperitoneal injection of urethane (1.25 g/kg) and held in the supine position. The degree of inhibition of pressor response to angiotensin (A) I was determined using these rats. The blood pressure was measured with a femoral artery cannula connected to a transducer (product of Nihon Kohden Kabushiki Kaisha, Japan, Model MPU-0.5-290-0-III) and recorded in terms of a mean blood pressure value through a carrier amplifier (product of Nihon Kohden Kabushiki Kaisha, Japan, Model RP-5) on a multipurpose polygraph (product of Nihon Kohden Kabushiki Kaisha, Japan, Model RM-85). The rats were set in an experimental device and left therein for 1 hour to stabilize the hemodynamics. Then experiments were commenced. Since the magnitude of the pressor response to AI varies with time, the ratio of the responses to AI and AII (AI/AII ratio) was used to determine the magnitude of the pressor response to AI which ratio remained more constant. Through the cannulated femoral vein, AI (300 ng/kg) was administered first and AII (300 ng/kg) was given in 5 minutes to measure an AI/AII ratio. At 30 minutes after the first administration of AI, AI (300 ng/kg) was similarly administered and AII (300 ng/kg) was given in 5 minutes, followed by measuring an AI/AII ratio. This procedure was repeated until a constant value of AI/AII ratio was obtained. (The mean value of AI/AII ratios each resulting from the repeated procedure is represented as "C" in an equation to be shown later). At 10 minutes after the final administration of AII, an aqueous solution containing 1 mg/kg of each test compound was given directly to the stomach through a vinyl tube. At 10 minutes after administration of the test compound, AI (300 ng/kg) was given and at 5 minutes later, AII (300 ng/kg) was administered, followed by measurement of the AI/AII ratio (which was represented as "E" in the following equation). An ACE percent inhibition was calculated according to the equation indicated below.

$$ACE \text{ Percent Inhibition} = \frac{C - E}{C} \times 100$$

Subsequently at each time of 60, 120 and 240 minutes after the administration of the test compound, AI (300 ng/kg) was given in the same manner as above and AII (300 ng/kg) was administered in 5 minutes, whereupon an ACE percent inhibition was calculated in the same way.

The results are shown below in Table 26 in which the test compounds listed are those prepared in the Examples indicated therein.

TABLE 26

| Test compound | Number of Animal | ACE Percent Inhibition (%) mean ± SD | | | |
|---|---|---|---|---|---|
| | | 15 min.* | 60 min.* | 120 min.* | 240 min.* |
| Ex. No. 5 | 6 | 28 ± 14 | 54 ± 3 | 54 ± 17 | 55 ± 7 |
| Ex. No. 18 | 7 | 77 ± 8 | 75 ± 23 | 84 ± 10 | 63 ± 6 |
| Ex. No. 21 | 5 | 22 ± 25 | 38 ± 29 | 58 ± 15 | 56 ± 14 |
| Ex. No. 32 | 6 | 15 ± 9 | 31 ± 7 | 33 ± 9 | 29 ± 8 |
| Ex. No. 39 | 7 | 39 ± 59 | 79 ± 30 | 76 ± 5 | 88 ± 3 |
| Ex. No. 40 | 6 | 37 ± 19 | 55 ± 18 | 57 ± 13 | 70 ± 9 |
| Ex. No. 42 | 5 | 27 ± 1 | 17 ± 18 | 57 ± 7 | 66 ± 7 |
| Ex. No. 67*[1] | 6 | 23 ± 35 | 55 ± 11 | 59 ± 4 | 63 ± 9 |
| Ex. No. 67*[2] | 7 | 46 ± 29 | 76 ± 10 | 61 ± 14 | 65 ± 7 |
| Ex. No. 71*[3] | 6 | 39 ± 34 | 65 ± 14 | 60 ± 2 | 67 ± 3 |
| Ex. No. 71*[4] | 7 | 47 ± 24 | 69 ± 6 | 70 ± 10 | 60 ± 10 |
| Ex. No. 81 | 5 | 14 ± 17 | 43 ± 18 | 47 ± 11 | 55 ± 6 |
| Control*[5] | 6 | 1 ± 5 | 6 ± 4 | 7 ± 6 | 9 ± 1 |

*Time after the administration of Test compound
*[1]L-arginine salt
*[2]maleate
*[3]L-arginine salt
*[4]maleate
*[5]N—[(S)—1-methoxycarbonyl-3-methylthiopropyl]-(R,S)—alanyl-(S)—proline hydrochloride (hydrochloride of the compound of Example 16 of Unexamined Japanese Patent Publication No. 81845/1980)

We claim:

1. A proline derivative represented by the formula

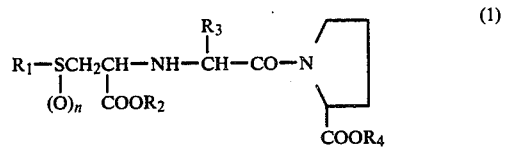

wherein:

$R_1$ is $C_5$-$C_{14}$ alkyl, $C_2$-$C_6$ alkenyl, $C_3$-$C_8$ cycloalkyl-$C_1$-$C_6$ alkyl or a group

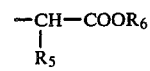

(wherein $R_5$ is hydrogen, $C_1$-$C_{14}$ alkyl or phenyl and $R_6$ is hydrogen or $C_1$-$C_6$ alkyl);
$R_2$ is hydrogen or $C_1$-$C_6$ alkyl;
$R_3$ is $C_1$-$C_6$ alkyl;
$R_4$ is hydrogen, $C_1$-$C_6$ alkyl or phenyl-$C_1$-$C_6$ alkyl; and
n is 0, 1 or 2,
and a pharmaceutically acceptable salt thereof.

2. A compound as defined in claim 1 wherein n is 0.

3. A compound as defined in claim 1 wherein n is 1 or 2.

4. A compound as defined in claim 2 wherein $R_1$ is $C_5$-$C_6$ alkyl.

5. A compound as defined in claim 2 wherein $R_1$ is $C_7$-$C_{14}$ alkyl.

6. A compound as defined in claim 2 wherein $R_1$ is a group

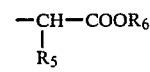

(wherein $R_5$ is hydrogen, phenyl or $C_1$-$C_{14}$ alkyl and $R_6$ is hydrogen or $C_1$-$C_6$ alkyl).

7. A compound as defined in claim 2 wherein $R_1$ is $C_2$–$C_6$ alkenyl or $C_3$–$C_8$ cycloalkyl-$C_1$–$C_6$ alkyl.

8. A compound as defined in claim 4 wherein $R_1$ is n-pentyl or n-hexyl.

9. A compound as defined in claim 8 wherein $R_2$ is hydrogen.

10. A compound as defined in claim 8 wherein $R_2$ is $C_1$–$C_6$ alkyl.

11. A compound as defined in claim 5 wherein $R_2$ is hydrogen.

12. A compound as defined in claim 5 wherein $R_2$ is $C_1$–$C_6$ alkyl.

13. A compound as defined in claim 11 or 12 wherein $R_1$ is n-heptyl or n-octyl.

14. A compound as defined in claim 6 wherein $R_1$ is a group

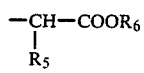

(wherein $R_5$ is hydrogen or phenyl and $R_6$ is hydrogen or $C_1$–$C_6$ alkyl).

15. A compound as defined in claim 6 wherein $R_1$ is a group

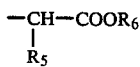

(wherein $R_5$ is $C_1$–$C_{14}$ alkyl and $R_6$ is hydrogen or $C_1$–$C_6$ alkyl).

16. A compound as defined in claim 14 or 15 wherein $R_6$ is $C_1$–$C_6$ alkyl.

17. A compound as defined in claim 7 wherein $R_2$ is $C_1$–$C_6$ alkyl.

18. A compound as defined in claim 3 wherein $R_1$ is $C_5$–$C_{14}$ alkyl or a group

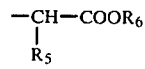

($R_5$ is hydrogen, phenyl or $C_1$–$C_{14}$ alkyl and $R_6$ is hydrogen or $C_1$–$C_6$ alkyl).

19. A compound as defined in claim 1 which is N-[(R)-1-ethoxycarbonyl-2-heptylthioethyl]-alanyl-(S)-proline ($\beta$-isomer).

20. A compound as defined in claim 1 which is methyl ester of N-[(R)-1-ethoxycarbonyl-2-heptylthioethyl]-alanyl-(S)-proline ($\beta$-isomer).

21. A compound as defined in claim 1 which is ethyl ester of N-[(R)-1-ethoxycarbonyl-2-heptylthioethyl]-alanyl-(S)-proline ($\beta$-isomer).

22. A compound as defined in claim 1 which is N-[(R)-1-ethoxycarbonyl-2-octylthioethyl]-alanyl-(S)-proline ($\beta$-isomer).

23. A compound as defined in claim 1 which is benzyl ester of N-[(R)-1-ethoxycarbonyl-2-heptylthioethyl]-alanyl-(S)-proline ($\beta$-isomer).

24. A compound as defined in claim 1 which is N-[(R)-1-ethoxycarbonyl-2-(1-ethoxycarbonylhexylthio)ethyl]-alanyl-(S)-proline (B-isomer).

25. A compound as defined in claim 1 which is N-[(R)-1-ethoxycarbonyl-2-(1-ethoxycarbonylheptylthio)ethyl]-alanyl-(S)-proline (B-isomer).

26. A compound as defined in claim 1 which is N-[(R)-1-ethoxycarbonyl-2-hexylthioethyl]-alanyl-(S)-proline ($\beta$-isomer).

27. A compound as defined in claim 1 which is N-[(R)-1-isobutyloxycarbonyl-2-heptylthioethyl]-alanyl-(S)-proline ($\beta$-isomer).

28. A pharmaceutical composition for inhibiting angiotension converting enzyme comprising at least one of the proline derivative and the pharmaceutically acceptable salt thereof as defined in claim 1 in an amount effective for inhibiting angiotension converting enzyme and a pharmaceutically acceptable carrier.

29. A method for inhibiting the angiotensin converting enzyme comprising administering to a patient at least one of the proline derivative and a pharmaceutically acceptable salt thereof as defined in claim 1 in an amount effective for inhibiting the angiotensin converting enzyme.

* * * * *